United States Patent
Rhoads et al.

(10) Patent No.: US 6,540,685 B1
(45) Date of Patent: Apr. 1, 2003

(54) ULTRASOUND DIAGNOSTIC DEVICE

(75) Inventors: Peter Koester Rhoads, Stow, MA (US); Edward C. Parnagian, Lowell, MA (US); Scott Barraclough, Gloucester, MA (US); Douglas E. Harriott, Melrose, MA (US); Janice M Blackwell-Jones, North Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 34 days.

(21) Appl. No.: 09/710,320

(22) Filed: Nov. 9, 2000

(51) Int. Cl.$^7$ ................................................ A61B 8/00
(52) U.S. Cl. ..................................................... 600/459
(58) Field of Search ........................ 600/437, 440–441, 600/443, 447, 459

(56) References Cited

U.S. PATENT DOCUMENTS 4,811,740 A * 3/1989 Ikeda et al. ................. 600/437

(List continued on next page.)

OTHER PUBLICATIONS

Terason 2000 information obtained from url: www.terason.com/terason2000.htm; 6 pages.
Sonosite 180 information obtained from url: www.sonosite.com/products_180_heart.html; 5 pages.
SonoHeart Applications Summary obtained from the SonoSite brochure; 2 pages.

Primary Examiner—Francis J. Jaworski
(74) Attorney, Agent, or Firm—John Vodopia

(57) ABSTRACT

An ultrasound diagnostic device is provided which is portable, small, light weight and easy to use. Preferably, the ultrasound diagnostic device is very small and light weight. The weight of the ultrasound diagnostic device normally will be approximately 6 or 7 pounds, including electrical control circuitry, a battery pack, a carrying strap and a transducer assembly. The ultrasound diagnostic device is similar in design to a laptop computer, except that it is smaller than typical laptop computers. The ultrasound diagnostic device comprises a console portion and a display portion. To open the device, the user simply flips open the display portion by lifting up on the display portion at a location near the front end of the device. The display portion is in a hinging relationship with the console portion so that when the user lifts up on display portion, the display portion is rotated upwards and away from the console portion. A transducer assembly is attached to the ultrasound diagnostic device and comprises a transducer cable, a transducer handle, a transducer and a transducer connector. The transducer connector comprises a latch which engages a mating mechanism comprised in a receptacle formed in the console portion. The connector enables different types of transducer assemblies to be implemented with the ultrasound diagnostic device, depending on the bodily feature being imaged. The ultrasound diagnostic device may be adapted to be harnessed with a carrying apparatus, e.g., a strap assembly, which enables the user to carry the device in a manner similar to the manner in which a person carries a camera around his or her neck. The user may operate the device when it is strapped to the user's body. The ultrasound device may include a handle to facilitate hand carriability.

31 Claims, 11 Drawing Sheets

U.S. PATENT DOCUMENTS

| | | | |
|---|---|---|---|
| 5,129,397 A | * 7/1992 | Jingu et al. | 600/437 |
| 5,268,817 A | * 12/1993 | Miyagawa et al. | 361/720 |
| 5,454,371 A | * 10/1995 | Fenster et al. | 600/443 |
| 5,590,658 A | 1/1997 | Chiang et al. | |
| 5,603,323 A | 2/1997 | Pflugrath et al. | |
| 5,636,631 A | 6/1997 | Waitz et al. | |
| 5,673,696 A | * 10/1997 | Bidwell et al. | 600/437 |
| 5,690,114 A | 11/1997 | Chiang et al. | |
| 5,699,803 A | * 12/1997 | Carodiskey | 600/437 |
| 5,715,823 A | 2/1998 | Wood et al. | |
| 5,722,412 A | * 3/1998 | Pflugrath et al. | 600/459 |
| 5,817,024 A | 10/1998 | Ogle et al. | |
| 5,839,442 A | 11/1998 | Chiang et al. | |
| 5,851,186 A | 12/1998 | Wood et al. | |
| 5,879,303 A | 3/1999 | Averkiou et al. | |
| 5,891,035 A | 4/1999 | Wood et al. | |
| 5,893,363 A | 4/1999 | Little et al. | |
| 5,897,496 A | 4/1999 | Canfield et al. | |
| 5,924,988 A | * 7/1999 | Burris et al. | 600/437 |
| 5,938,607 A | 8/1999 | Jago et al. | |
| 5,957,846 A | 9/1999 | Chiang et al. | |
| 5,964,709 A | * 10/1999 | Chiang et al. | 600/437 |
| 5,997,479 A | 12/1999 | Savord et al. | |
| 6,007,490 A | 12/1999 | Pawluskiewicz | |
| 6,013,032 A | 1/2000 | Savord | |
| 6,102,863 A | 8/2000 | Pflugrath et al. | |
| 6,106,468 A | 8/2000 | Dowdell | |
| 6,106,472 A | 8/2000 | Chiang et al. | |
| 6,113,547 A | 9/2000 | Catallo et al. | |
| 6,117,084 A | 9/2000 | Green et al. | |
| 6,117,085 A | 9/2000 | Picatti et al. | |
| 6,126,608 A | * 10/2000 | Kemme et al. | 600/459 |
| 6,135,961 A | 10/2000 | Pflugrath et al. | |
| 6,238,344 B1 | * 5/2001 | Gamelsky et al. | 600/437 |
| 6,251,073 B1 | * 6/2001 | Imran et al. | 600/443 |

* cited by examiner

ULTRASOUND DIAGNOSTIC DEVICE

TECHNICAL FIELD OF THE INVENTION

The present invention relates to an ultrasound diagnostic device and, more particularly, to an ultrasound diagnostic device which is very small, light-weight, portable, and capable of being used in virtually any type of environment and with greater flexibility than other ultrasound diagnostic devices currently available on the market.

BACKGROUND OF THE INVENTION

Portable ultrasound systems are known in the ultrasound equipment industry. Although the known portable ultrasound systems have been designed to facilitate ease of use and portability, none of the known systems provide a total solution in terms of ergonomics, ease of use, and display image quality. For example, a system might be easy to carry because it is relatively small, but cumbersome to operate due to the fact that the user must manipulate the ultrasound transducer with one hand, which in some cases is a rather bulky piece of equipment, while holding the ultrasound diagnostic device in the other hand. Even if the user does not hold the ultrasound diagnostic device, but rather, places it on a stable surface, the user may have difficulty viewing the image due to limitations relating to the adjustability of the display.

To provide another example, even if the ultrasound diagnostic device has good adjustability with respect to the display, the enclosure may be designed such that it must be placed on a relatively stable, flat surface when not being held by the user. In some environments, such as at the scene of an automobile accident, a stable, flat surface may not be available. This may result in the user having to hold the ultrasound diagnostic device in one hand while using the other hand to manipulate the transducer of the ultrasound diagnostic device. This prevents the user from being able to use a hand to steady the user while obtaining diagnostic measurements, which may be important in certain environments.

For example, Chang, U.S. Pat. No. 5,738,099, issued Apr. 14, 1998, discloses an ultrasound diagnostic device which has a pistol-shaped housing. A small, liquid crystal display is installed in the back end of the housing and a transducer is located on the muzzle of the device. The user holds the device like a pistol when obtaining measurements. Although the Chang patent states that the device is small in volume and light-weight, the display is also very small and is not adjustable. Therefore, the image display quality provided by this device is very limited.

Chiang, et al., U.S. Pat. No. 5,690,114, issued Nov. 25, 1997, discloses a portable ultrasound imaging system which is comprised in the form of either a lap top computer, a personal computer (PC) or other type of computer, or a single-piece hand-held device. If a PC or other type of computer is used, it is connected to a cathode ray tube for displaying the ultrasound images. Such a system would be relatively heavy and large in volume and, consequently, not easy for a user to transport. Although lap top computers are relatively small and light weight in comparison to PCs, lap top computers are still relatively large in size due in part to the fact that they implement a full keyboard.

Also, although lap top computers are relatively small in size, there is no disclosure in the Chiang patent of any provision for facilitating carrying the lap top computer or for supporting it on the user's body when it is being operated.

Although the Chiang patent mentions that the system can be comprised as a single-piece hand-held device, there is no further discussion in the patent of this embodiment. Furthermore, since the hand-held device would be comprised as a single piece, there presumably would be no provision for adjusting the angle or position of the display.

Pflugrath, et al., U.S. Pat. No. 5,722,412, issued Mar. 3, 1998, discloses a hand-held ultrasound diagnostic instrument which can be comprised as a single-piece unit or as two separate sections. The Pflugrath patent states that the single-piece unit is less than five pounds. The single-piece unit is 20.3 cm high, 11.4 cm wide and 4.5 cm deep. The single-piece unit has an upper portion and a lower portion with the upper portion comprising the display and the lower portion comprising the user controls. Since the unit is comprised as a single piece, the display cannot be positionally adjusted. Furthermore, since the width of the device is very small, the display will also be very small, which limits the image display quality. Also, since the transducer is located in the bottom portion of the unit, the entire unit must be manipulated in order to obtain ultrasound images from the patient's body. Thus, the ability to view the display will be limited by the positioning of the device to ensure that a suitable image is obtained from the patient.

With respect to the two-unit device disclosed in the Pflugrath patent, the upper unit is connected to the lower unit by a cable. The upper unit comprises the display and the lower unit comprises the user controls. As with the single-piece unit, the transducer is located in the lower portion. The user obtains an image from the patient's body by using one hand to place the lower portion at an appropriate location on the patient's body and by using the other hand to hold the upper portion at a suitable viewing position. Therefore, the user is unable to manipulate the controls while obtaining an ultrasound image because both hands are occupied for the purpose of holding the upper and lower portions. All of these shortcomings adversely affect the ease of use and image display quality of the device.

These are only examples of some of the shortcomings of known portable ultrasound diagnostic systems. These examples demonstrate that none of the known systems provide an overall solution in terms of ergonomics, ease of use and image display quality. Accordingly, a need exists for a portable ultrasound diagnostic device which meets all of these goals.

SUMMARY OF THE INVENTION

The present invention provides an ultrasound diagnostic device for acquiring and processing ultrasound images. The device comprises a console portion and a display portion which are coupled together to allow the display portion to be positionally adjusted with respect to the console portion. The console portion comprises a control panel which comprises a plurality of input keys. A user may input commands on the control panel by actuating one or more keys on the control panel. The console portion comprises electrical control circuitry which receives electrical signals from the control panel which correspond to commands entered by the user on the control panel. The electrical control circuitry processes the electrical signals and performs operations on an ultrasound image being displayed on a display monitor. The ultrasound images being displayed on the display monitor may be modified by the electrical control circuitry in response to one or more keys of the control panel being actuated by the user. A transducer receptacle disposed on the console portion allows a transducer assembly to be connected to the console portion. The transducer assembly comprises a transducer, a cable and a connector, which can be used by the user to acquire ultrasound image information from a subject.

Preferably, the ultrasound diagnostic device is extremely light-weight. The transducer receptacle is adapted to allow the transducer assembly to be easily connected to and disconnected from the transducer receptacle. This allows different transducer assemblies which may be used for performing different types of ultrasound imaging tasks to be utilized with the ultrasound diagnostic device of the present invention.

The ultrasound diagnostic device may be adapted to allow a strap assembly to be connected to the ultrasound diagnostic device. The strap assembly is designed to allow the ultrasound diagnostic device to be carried over the shoulder of the user or to be placed around the neck of the user. When placed about the neck of the user, the ultrasound diagnostic device is maintained by the strap assembly in a position which is substantially parallel to the floor. In this position, the control panel and the display monitor are disposed so that the ultrasound diagnostic device can be fully operated by the user. This feature of the present invention maximizes the ergonomics and ease of use of the ultrasound diagnostic device.

The ultrasound diagnostic device may be equipped with a handle to enable the device to be easily carried by hand. The ultrasound device may be configured to store images in a standard format, such as the JPEG or TIFF formats, for example, so that the images can easily be archived, viewed, printed, etc., by a home user.

Preferably, the ultrasound diagnostic device is comprised in the form of a lap top computer, but is significantly smaller than typical lap top computers. The display portion of the ultrasound diagnostic device can be positionally adjusted with respect to the control panel portion in the same manner in which the display portion of a typical lap top computer can be adjusted. The display portion remains in place until the user re-adjusts it. This feature of the present invention facilitates viewing of the image be the user, thereby enhancing overall image display quality.

These and other features and advantages of the present invention will become apparent from the following description, drawings and claims.

DETAILED DESCRIPTION OF THE INVENTION

Figure 1:
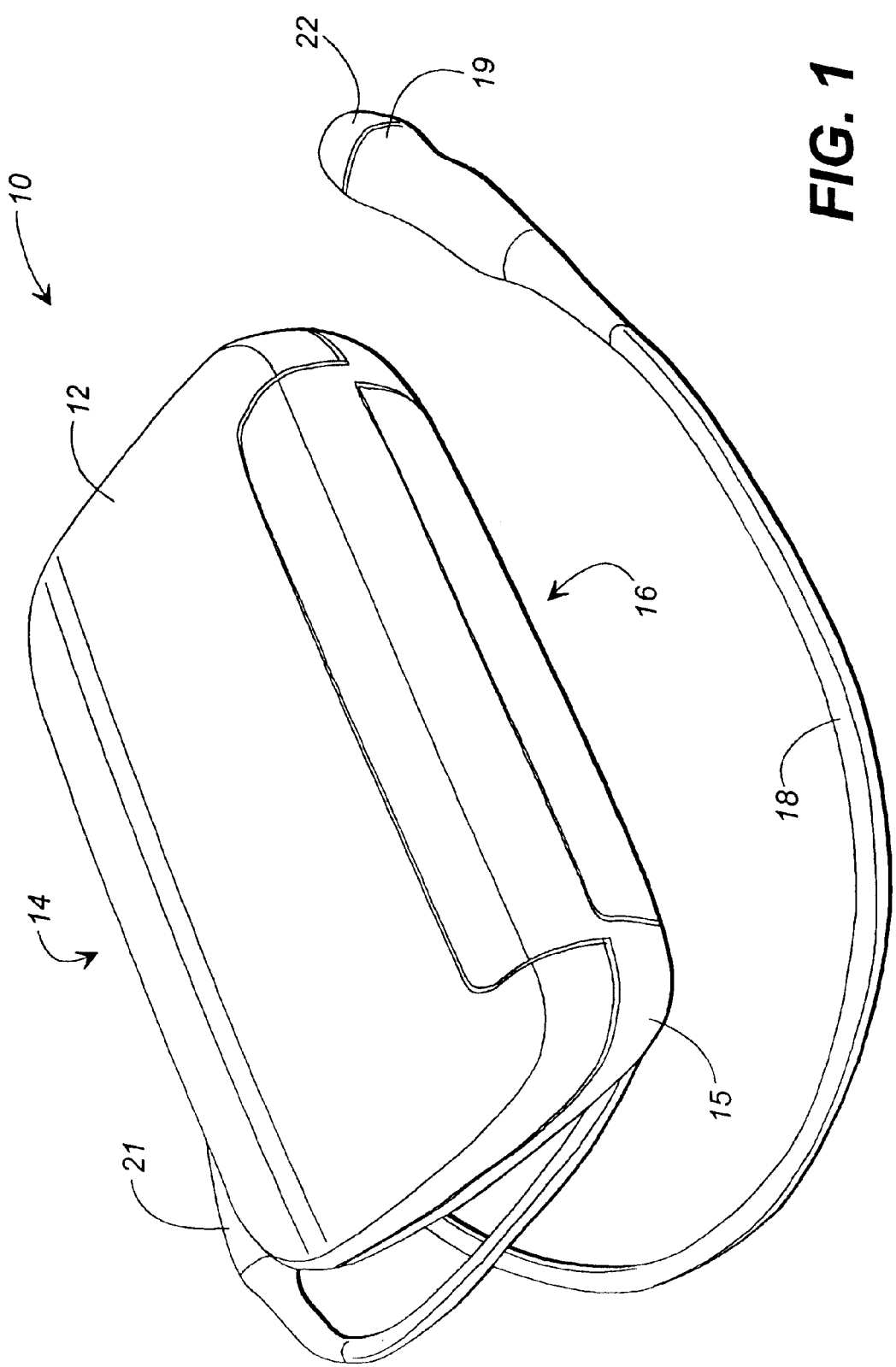
FIG. 1 is a top, perspective view of the ultrasound diagnostic device of the present invention.

FIG. 1 is a pictorial representation of the ultrasound diagnostic device 10 in accordance with one embodiment of the present invention. The ultrasound diagnostic device 10 shown in FIG. 1 preferably is 10½ inches long, 8 inches wide and 2 ¾ inches thick, although those skilled in the art will understand that the present invention is not limited to these exact dimensions. The weight of the device 10 preferably will be less than 6 pounds, including the electrical control circuitry, the battery pack, the carrying strap and the transducer assembly, which are all discussed below in detail. The manner in which this light-weight design has been achieved in accordance with the present invention is attributable to the overall design and construction of the device 10 and to the judicious selection of electrical and data storage components implemented in the device 10, as discussed below in more detail.

The device 10 is similar in design to a laptop computer, except that it preferably is smaller than typical laptop computers. The device 10 comprises a console portion 15 and a display portion 12. To open the device 10, the user simply flips open the display portion 12 by lifting up on the display portion 12 at a location near the front end 14 of the device 10. The display portion 12 is in a hinging relationship with the console portion 15 so that when the user lifts up on display portion 12, the display portion 12 is rotated upwards (i.e., away from the console portion 15). The hinging relationship is provided by a hinging mechanism (not shown) which couples the display portion 12 to the console portion 15 at one or more locations adjacent the back end 16 of the ultrasound diagnostic device 10. The hinging mechanism may be similar to hinging mechanisms typically used with laptop computers currently available on the market. When the display portion 12 has been placed at a particular viewing position, the display portion 12 will remain in the viewing position until it is re-adjusted by the user. This feature facilitates viewing of the ultrasound image by the user, which enhances the overall image display quality provided by the device.

A transducer assembly preferably is removably connected to the ultrasound diagnostic device 10 and comprises a transducer cable 18, a transducer handle 19, a transducer 22 and transducer connector 21. The transducer connector 21 removably connects the end of the cable 18 to the console portion 15. The connector 21 comprises a latch (not shown) which engages a mating mechanism (not shown) comprised in a receptacle formed in the console portion 15. Preferably, the transducer handle 19 is small enough to fit comfortably in the palm of the hand of the user so that it can be easily manipulated by a user.

The connector 21 enables different types of transducer assemblies to be implemented with the ultrasound diagnostic device 10. Depending on the bodily feature being imaged, different transducer assemblies can be utilized with the ultrasound diagnostic device 10. The user can easily unplug one type of transducer assembly and easily plug another transducer assembly into the receptacle. Of course, each transducer assembly must be adapted to mate with the receptacle. This provides the ultrasound diagnostic device 10 with great flexibility with respect to its applications, as will be understood by those skilled in the art. For example, the ultrasound diagnostic device 10 may be used by a cardiologist doing rounds at a hospital. Rather than using a stethoscope to check patients' heart beats, the cardiologist may connect the appropriate transducer assembly to the device 10 and use the device 10 in the same manner in which a conventional stethoscope is used. In contrast, the ultrasound diagnostic device may be used by a gynecologist to perform fetal monitoring, in which case, a transducer assembly suitable for that purpose will be plugged into the receptacle.

As described in more detail below, the ultrasound diagnostic device 10 is adapted to be harnessed with a carrying apparatus, e.g., a strap assembly, which enables the user to carry the device 10 in a manner similar to the manner in which a person carries a camera around his or her neck. The user may, but is not required, to use the device 10 when it is strapped to the user's body, as described below in detail. Alternatively, the user may, for example, remove the device 10 from his or her body, set it on a patient's bed, rotate the display portion 12 to an appropriate viewing position, turn on the device 10, and manipulate the transducer handle 19 to image the patient's heart. The advantages of this carrying feature of the present invention will become apparent from the discussion provided below with respect to FIGS. 2 and 4.

When the ultrasound diagnostic device 10 is intended to be used with transducer assemblies that are implemented for different imaging purposes, the ultrasound diagnostic device 10 comprises software and/or hardware that is capable of acquiring and processing the various types of imaging information. The ultrasound diagnostic device 10 may be switched between imaging modes which correspond to different transducer assemblies. In this case, the ultrasound diagnostic device may comprise different software driver modules for each of the different transducer assemblies.

The ultrasound diagnostic device 10 comprises a central processing unit (not shown), e.g., a microprocessor, which controls the operations of the ultrasound diagnostic device 10. When the user switches from one mode to another, the central processing unit (CPU) simply executes the appropriate software module to enable the central processor to acquire and process the image data obtained by the transducer assembly, as will be understood by those skilled in the art. The software modules may be stored in a system memory device (not shown) which is in communication with the CPU. Alternatively, whenever a particular transducer assembly is to be used, the user can load an appropriate software driver module into the system memory device via some type of data input device (not shown), such as, for example, a magnetic disk or CD ROM drive.

Figure 2:
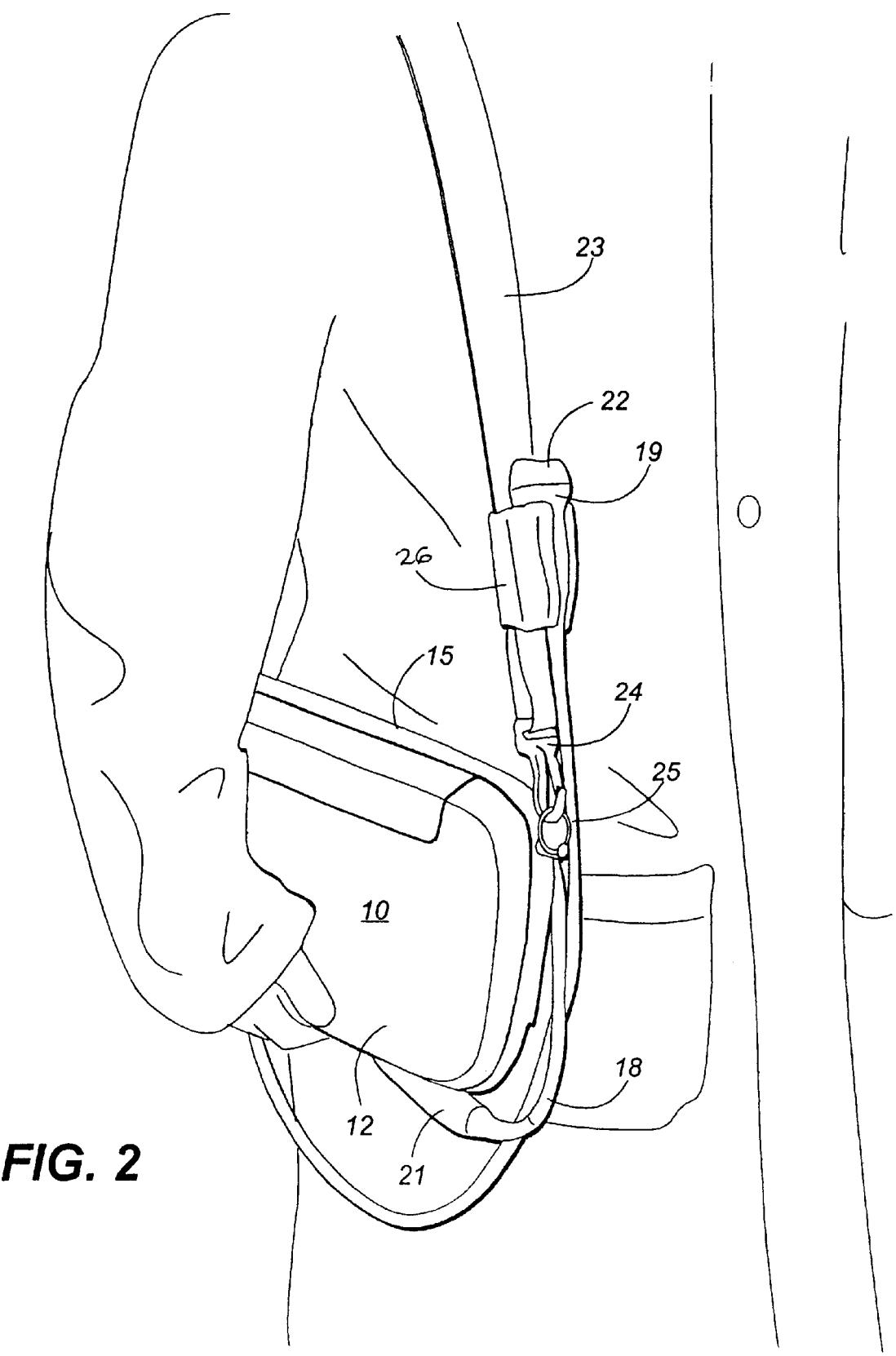
FIG. 2 is a perspective view of the ultrasound diagnostic device of FIG. 1 being carried on the shoulder of a user.

As shown in FIG. 2, the transducer 22 of the transducer assembly preferably is carried in a holster 26, which preferably is made of a soft, rubber-like material. The holster 26 assists in preventing the transducer 22 from colliding with objects and people. The holster 26 maintains the transducer 22 in a position close to the user's body to thereby prevent it from being disposed to collide with objects. Since transducers of the type used to perform ultrasound diagnostic measurements are typically very sensitive and relatively expensive, it is important to protect the transducer 22.

It is also important to protect the transducer cable 18 from damage. Hanging transducer cable loops can snag on objects, such as, for example, doorknobs. In accordance with the preferred embodiment of the present invention, the transducer cable 18 is stored by wrapping the cable 18 around the console portion 15, between a handle (not shown) and the console portion 15, and around a flange (not shown) comprised by the device 10, preferably in a single loop, and by securing the transducer handle 19 in the holster 26. This feature protects the transducer cable 18, as well as the transducer connector 21 and the transducer 22. The handle is optional and is discussed below with respect to FIG. 7.

There are several alternative methods and apparatuses for storing the transducer cable 18. For example, a spring-take-up method, similar to that used with vacuum cleaners to store vacuum cleaner cords, may be used with the present invention. In this case, the holster 26 may be mounted on the enclosure. Another alternative is to use a transducer cable which is spirally wound, similar to a conventional telephone cord. Another alternative is to use a spring-loaded pulley take-up disposed near or at the midpoint of the transducer cable. Those skilled in the art will understand how each of these alternative techniques may be implemented with the present invention.

In FIG. 2, the ultrasound diagnostic device 10 is shown as being carried on the shoulder of a user. The strap assembly 23 is removably attached to the device 10 by a fastening mechanism 24, such as, for example, a clip which clips onto a ring 25. In this case, the ring is fixedly secured to the console portion 15. A similar fastening mechanism and ring (not shown) may be used to attach the other end (not shown) of the strap assembly 23 to the opposite side of the ultrasound diagnostic device 10. The shoulder strap assembly 23 may be easily removed by unclipping the clips from the rings 25. The rings may be attached to the console portion 15 by any suitable fastening mechanism.

An alternative fastening mechanism that may be used for attaching the strap assembly 23 to the console portion 15 is a cylindrical latch (not shown) with a spring-loaded barbed plunger (not shown). With this type of attachment mechanism, when the user presses in on an end-mounted, spring-loaded, barbed plunger, a retaining bar is released, which allows the barbed plunger to be released and removed from the cylinder. When using this type of mechanism, the barbed plunger portion may be attached to the ends of the strap assembly 23 while the cylinder may be attached to the console portion 15. It will be understood by those skilled in the art that the present invention is not limited to any particular arrangement or device for attaching the shoulder strap assembly 23 to the ultrasound diagnostic device 10.

Figure 3:
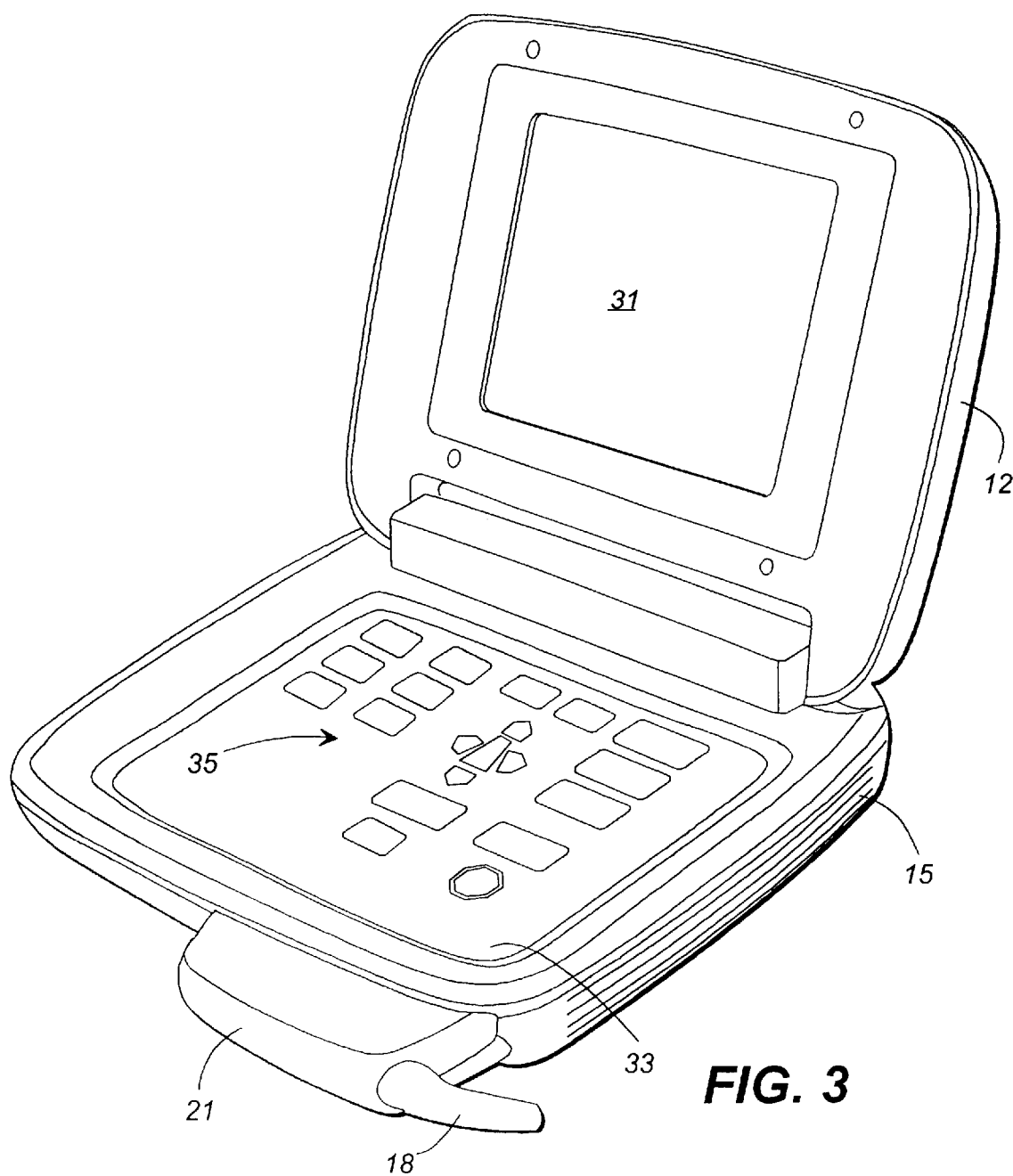
FIG. 3 is a pictorial representation of the ultrasound diagnostic device shown in FIG. 1 with the display screen placed in a viewing position.

FIG. 3 illustrates the ultrasound diagnostic device 10 with the display portion 12 placed in a viewing position. Preferably, the display screen 31 comprised by the display portion 12 is a full-color liquid crystal display (LCD) screen, which preferably is approximately 6.4 inches across the diagonal of the screen 31. As will be understood by those skilled in the art, the screen 31 is not limited to any particular dimensions. The console portion 15 comprises a small control panel 33 having keys 35, which have icons on them. By using icons on the keys, a single control panel 15 can be used in different countries around the world because the icons have been selected so that the meanings of the icons generally are well known to those who perform ultrasound diagnostic imaging tasks, as will be understood by those skilled in the art. The icons will be discussed in more detail below with reference to FIG. 6.

Figure 4:
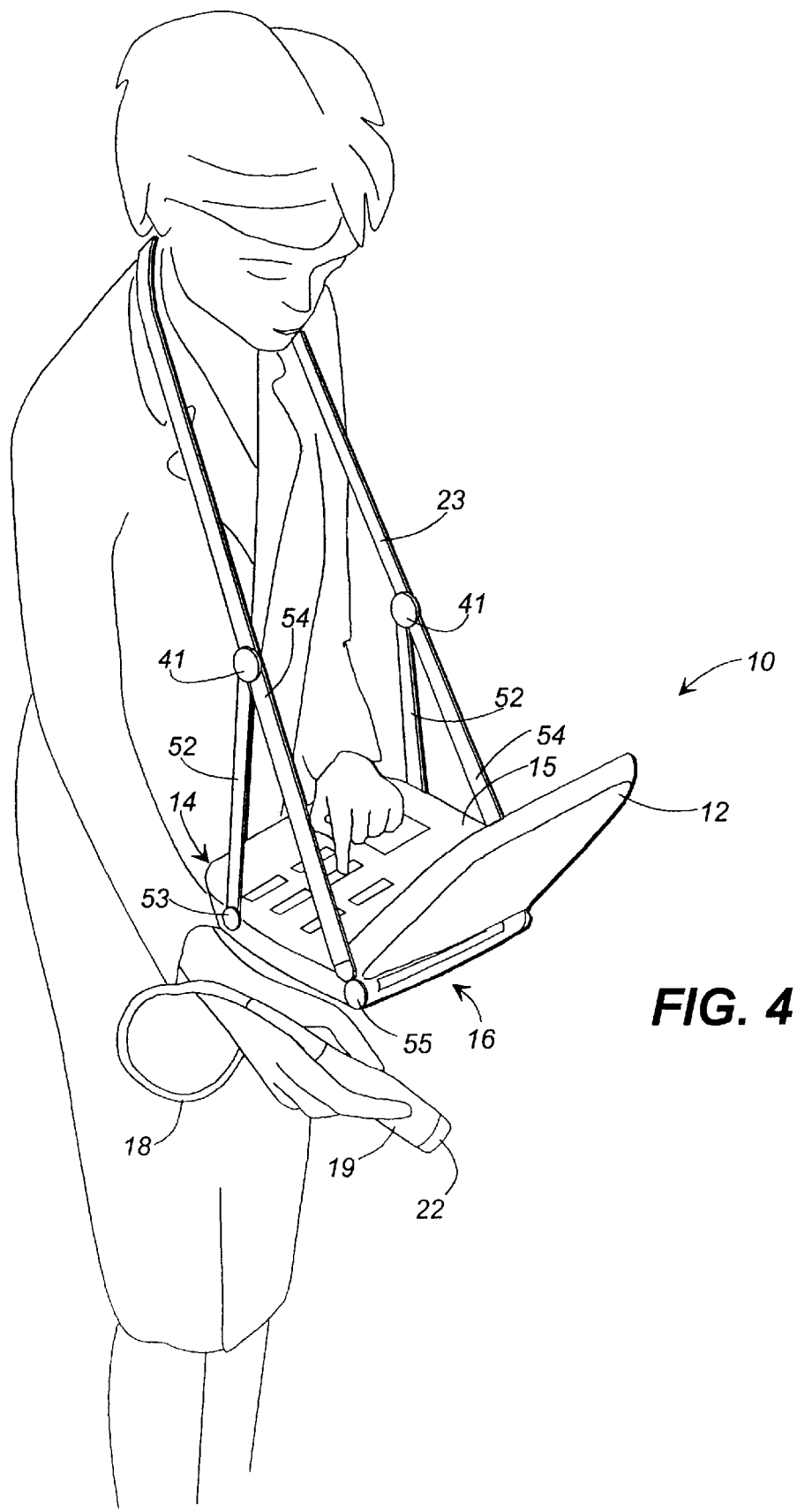
FIG. 4 is a pictorial representation of the ultrasound diagnostic device shown in FIG. 1 wherein the strap assembly is fully supporting the ultrasound diagnostic device when the device has been placed in an operable mode while standing.

FIG. 4 illustrates the ultrasound diagnostic device 10 wherein the strap assembly 23 is fully supporting the ultrasound diagnostic device 10 when it has been placed in an operable mode. The strap assembly 23 preferably forks at fastening devices 41 and front portions 52 of the strap assembly 23 attach by fastening devices 53 to the front end 14 of the console portion 15. Back portions 54 of the strap assembly 23 attach by fastening devices 55 to the back end 16 of the console portion 15. The fastening devices 53 and 55 may be identical to the fastening mechanisms discussed above with respect to FIG. 2. As will be understood by those skilled in the art, the device 10 is not limited to any particular fastening devices for performing this function. Also, the present invention is not limited with respect to the locations at which the strap assembly 23 attaches to the device 10, as will be understood by those skilled in the art.

The strap assembly 23 allows the user to perform diagnostic measurement tasks when walking, standing or sitting. When the user is carrying the device 10 in the manner shown in FIG. 2, the strap assembly 23 collapses into a simple shoulder strap, as shown in FIG. 2. When the device 10 is going to be carried on the user's shoulder, the front and rear portions 52 and 54 of the strap assembly 23 may be secured to the strap assembly 23 so that they will not dangle freely. This can be accomplished by any suitable mechanism, such as, for example, a hook-and-loop material (e.g., Velcro) placed on the strap assembly at suitable locations, as will be understood by those skilled in the art. A handle (not shown) may also be attached to the console portion 15 to enable the user to carry the device 10 by hand.

Figure 5:
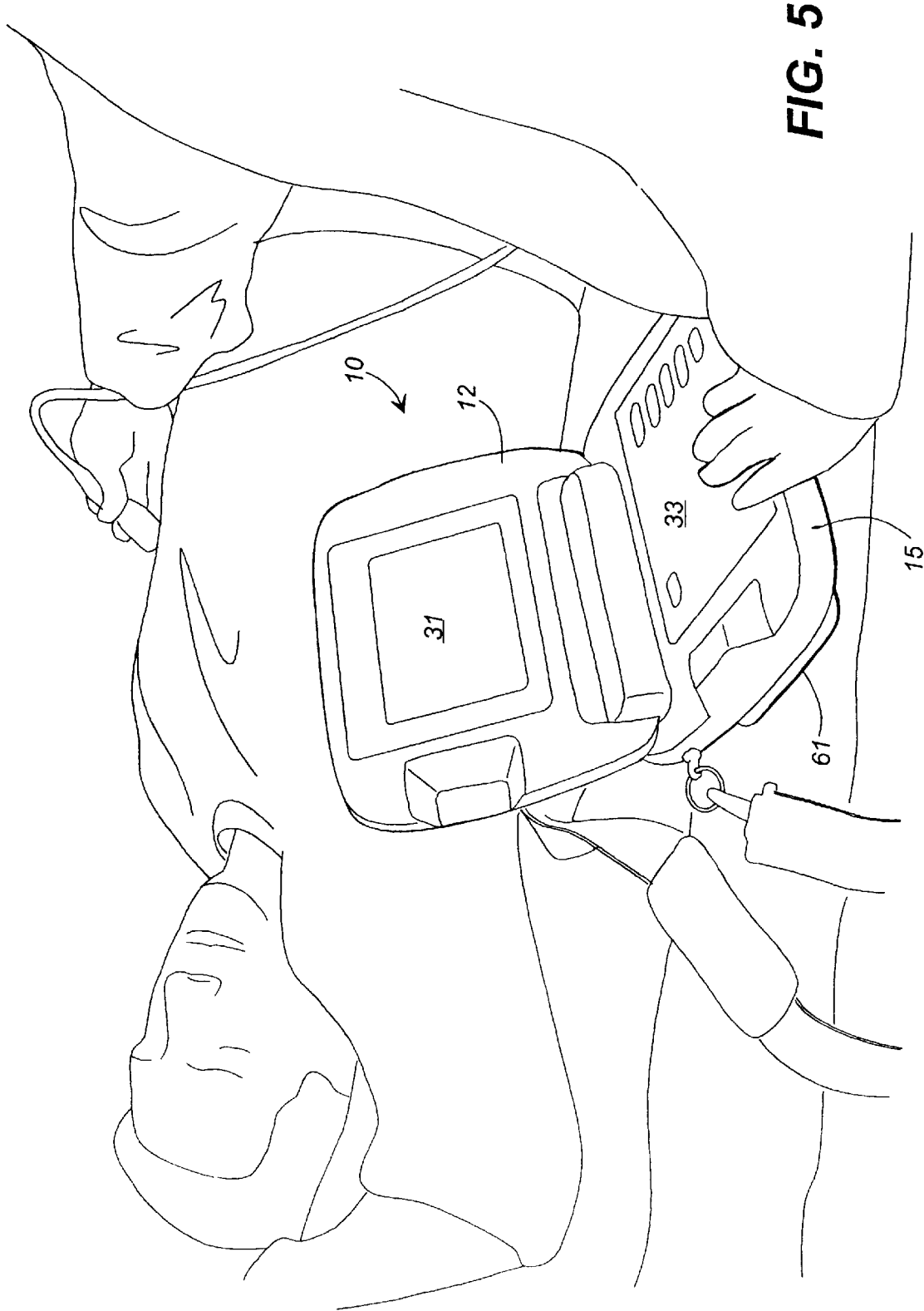
FIG. 5 is pictorial representation of the ultrasound diagnostic device shown in FIG. 1 when it has been removed from the user's body and placed on a surface, such as the bed of the patient, when the user is performing diagnostic measurements.

As shown in FIG. 5, the ultrasound diagnostic device 10 may be removed from the user's body and placed on a surface, such as the bed of the patient, when the user is performing diagnostic measurements. Preferably, the device 10 comprises a non-skid pad (not shown) which is affixed to one or more locations on the bottom surface of the device 10. The non-skid pad inhibits movement of the device 10 when it is placed on slanted and/or slick surfaces. This is advantageous in emergency situations where the environment or settings may not provide ideal surfaces. For example, the user may need to place the device 10 on the hood of a car in the rain. In such a situation, the non-skid pad inhibits movement of the device 10. A flange 61 preferably is attached to the bottom surface of the console portion 15 for the purpose of allowing the transducer cable 18 to be wrapped about the console portion and seated in the flange 61.

The flange 61 and the side of the console portion 15 form a U-shaped retainer for receiving and holding the transducer cable 18 in place adjacent the side of the console portion 15. Preferably, the distance between the top of the flange and the side of the console portion 15 is slightly smaller than the width of the transducer cable 18 such that the transducer cable 18 is snapped into the retainer formed by the side of the console portion 15 and the flange 61. However, preferably the distance between the flange and the console portion 61 at the bottom of the retainer, i.e., where the cable 18 is seated, is slightly larger than the diameter of the cable 18 so as not to damage the cable 18.

Preferably, the display portion 12 and the console portion 15 are comprised of cast metal and molded plastic to provide the ultrasound diagnostic device 10 with a rugged encasement. The ultrasound diagnostic device 10 is designed to withstand external impact resulting from, for example, dropping the device 10 or collisions between the device 10 and external objects. Furthermore, the ultrasound diagnostic device 10 folds, as described above, such that when it is not in use the display screen 31 and the control panel 33 are protected from external forces. The transducer connector 21 is also designed of the same or similar types of materials so that it can also withstand shocks from external forces. These features of the ultrasound diagnostic device 10 ensure reliability and reduce the possibility of damaging the device 10 in the field, which is especially important in emergency situations. Also, by increasing the reliability of the instrument, maintenance servicing requirements are reduced, thereby potentially increasing cost savings.

Figure 6:
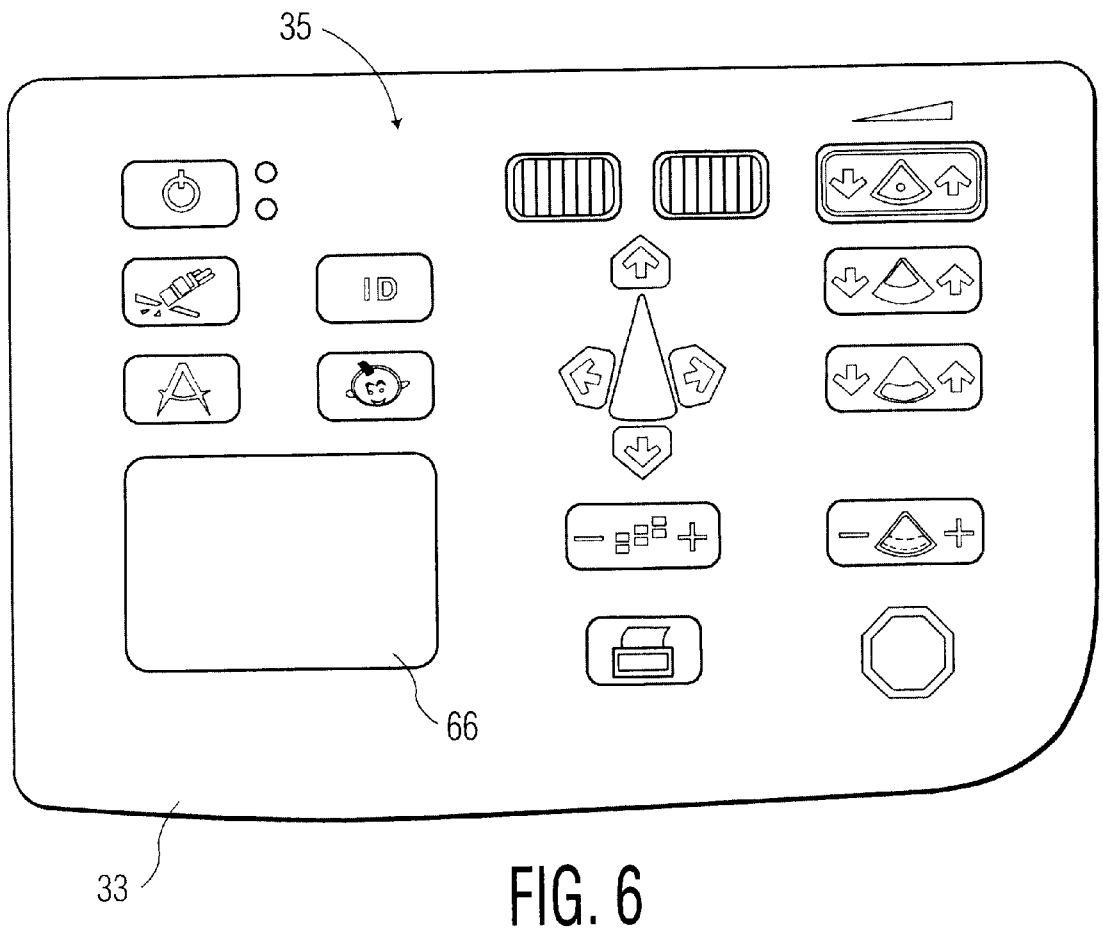
FIG. 6 is a top view of the control panel of the ultrasound diagnostic device of FIG. 1, which illustrates the icons located on the input keys.

FIG. 6 is a top view of the control panel 33 of the ultrasound diagnostic device 10. As shown in FIG. 6, icons have been placed on the keys 35 of the control panel to facilitate ease of use of the device 10 by users. In accordance with this embodiment, all system controls are "one button-one function", i.e., each key corresponds to a command which tells the central processor to perform a particular function. The keys preferably are logically and ergonomically grouped in such a manner that they can be easily identified and so that their meanings are self-evident to persons skilled at performing ultrasound imaging tasks. The keys, or controls, can be illuminated on demand by the user by activating a switch (not shown) on the control panel 33. Alternatively, the ultrasound diagnostic device 10 may comprise a light sensor which senses the level of illumination and which causes the controls to be illuminated when the level of illumination drops below a predetermined level.

A touch sensitive cursor control pad 66 is preferably comprised by the control panel 33 to allow a user to navigate various screen menus and tables when performing image measurements. Other types of digitizing devices can be used for this purpose, such as, for example, a track ball, a joy stick, a display screen touch overlay, etc., as will be understood by those skilled in the art. However, it has been determined that a touch sensitive cursor control pad is the best tool for performing these functions. Other pointing devices, such as trackballs and mice, for example, comprise moving parts. When obtaining ultrasound images from a patient, technicians' hands are usually covered with a jelly-like substance, which functions as an ultrasound compliant between a patient's body and the transducer. This substance can enter the pointing devices that have moving parts and adversely affect the operations of the pointing devices. By using a control pad which does not have any moving parts and which is sealed from the environment, the possibility of this substance entering and adversely affecting the pointing device is eliminated.

Figure 7:
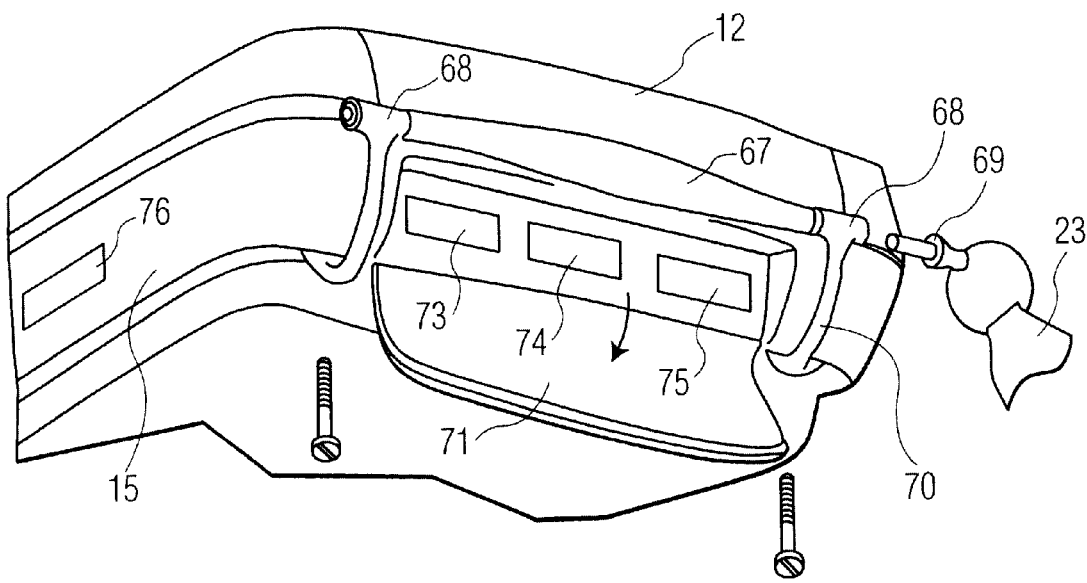
FIG. 7 is a rear view of the ultrasound diagnostic device of FIG. 1, which shows an attachment assembly for attaching the strap assembly to the ultrasound diagnostic device.

FIG. 7 is a rear view of the ultrasound diagnostic device 10, which shows the preferred attachment assembly for attaching the fastening mechanism discussed above with respect to FIG. 2 to the device 10. In accordance with this embodiment, the strap assembly 23 can be removably attached to the console portion 15 via the spring-loaded latch and barbed plunger discussed above with respect to FIG. 2. The cylindrical portion 68 of the fastening mechanism preferably is housed in the handle 67 of the ultrasound diagnostic device 10. The handle 67 may be used by a user to hand-carry the ultrasound diagnostic device 10. The plunger portion 69 of the attachment mechanism can be easily removed from the cylindrical portion 68 in the manner discussed above with respect to FIG. 2, thereby disconnecting the strap assembly 23 from the ultrasound diagnostic device 10. When the transducer cable 18 is wrapped about the device 10, the cable 18 (not shown) rests against the J-shaped elements 70 which connect the handle 67 to the console portion 15.

A rear cover panel 71, which can be opened and closed to allow various data storage and transmission devices to be connected to the ultrasound diagnostic device via ports 73, 74, 75 and 76. For example, one of the ports 73 may be used with a network connection (not shown) to enable data to be loaded into and downloaded from the ultrasound diagnostic device 10. One of the ports 74 may be used for an infrared receiver and transmitter diode pair, which is used to establish an optical data path between the ultrasound device, and a computer (not shown), printer (not shown), network connection (not shown), or mass storage device (not shown). Another port 75 may be used as an alternative, non-optical means to allow, for example, a computer or printer (not shown) to be connected to the ultrasound diagnostic device 10 to enable data to be loaded into and downloaded from the ultrasound diagnostic device 10. Port 76, which is located on the side of the console portion 15, preferably is adapted to receive a compact flash memory card, as is described below in detail.

Figure 8:
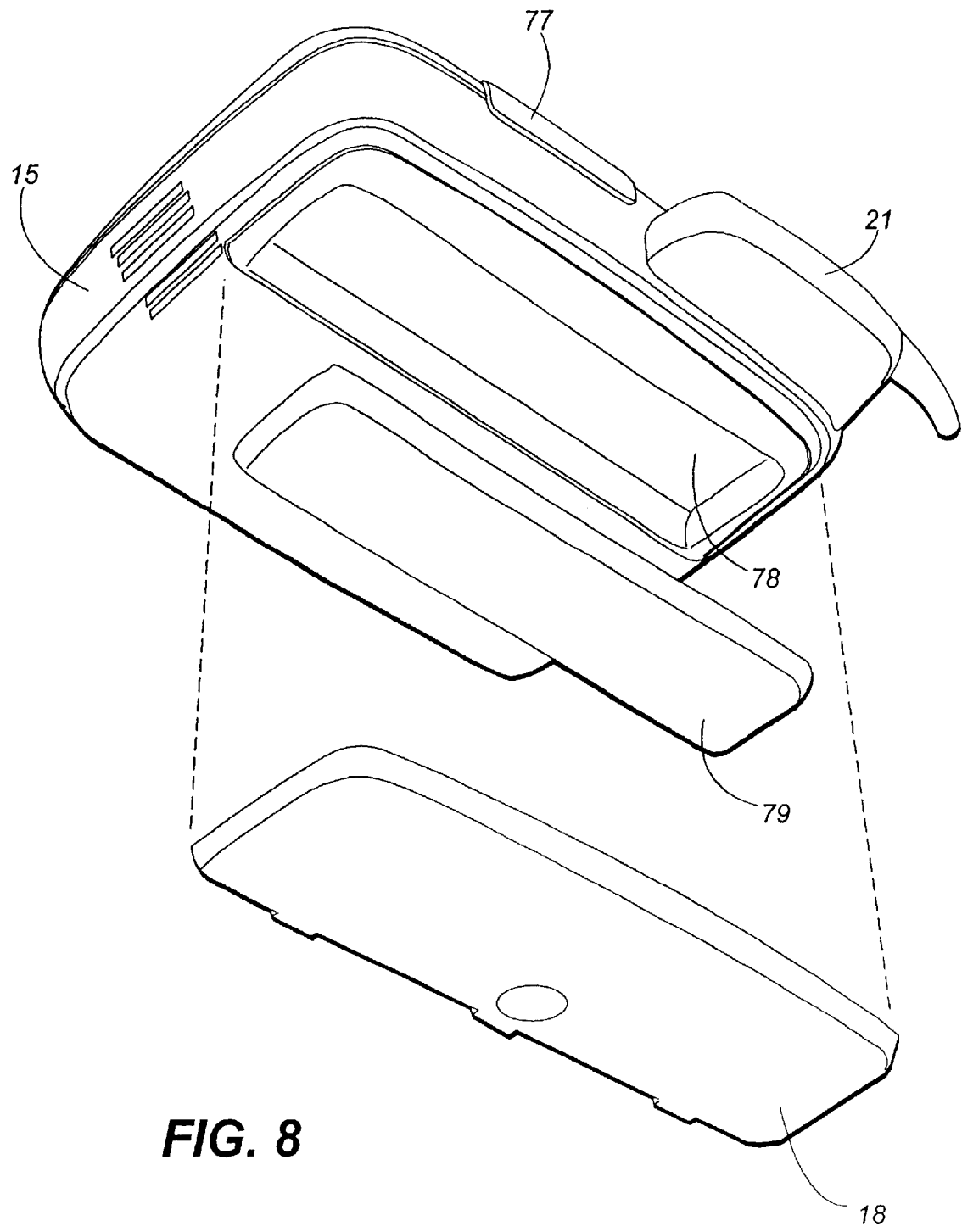
FIG. 8 is a bottom view of the ultrasound diagnostic device of FIG. 1, which illustrates the battery well and a battery located in the battery well.

FIG. 8 is a bottom view of the ultrasound diagnostic device 10. The console portion 15 comprises a latch 77 for securing the display portion 12 in the closed position adjacent the console portion 15. The display portion 12 has a mechanism (not shown) which mates with the latch 77. The display portion 12 can be unlatched from the console portion 15 by simply applying a sufficient amount of force to latch 77 to separate the display portion 12 from the console portion 15. A battery well 78 located in the bottom of the console portion 15 is designed to receive rechargeable battery 79. A removable battery cover 81 mates with the opening 78 of the battery well to maintain the rechargeable battery 79 within the battery well. Preferably, a recharger (not shown) can be used to recharge the battery while the battery is supplying power to the ultrasound diagnostic device 10. Rechargers and batteries that provide this capability are currently available on the market, as will be known to those skilled in the art.

Figure 9:
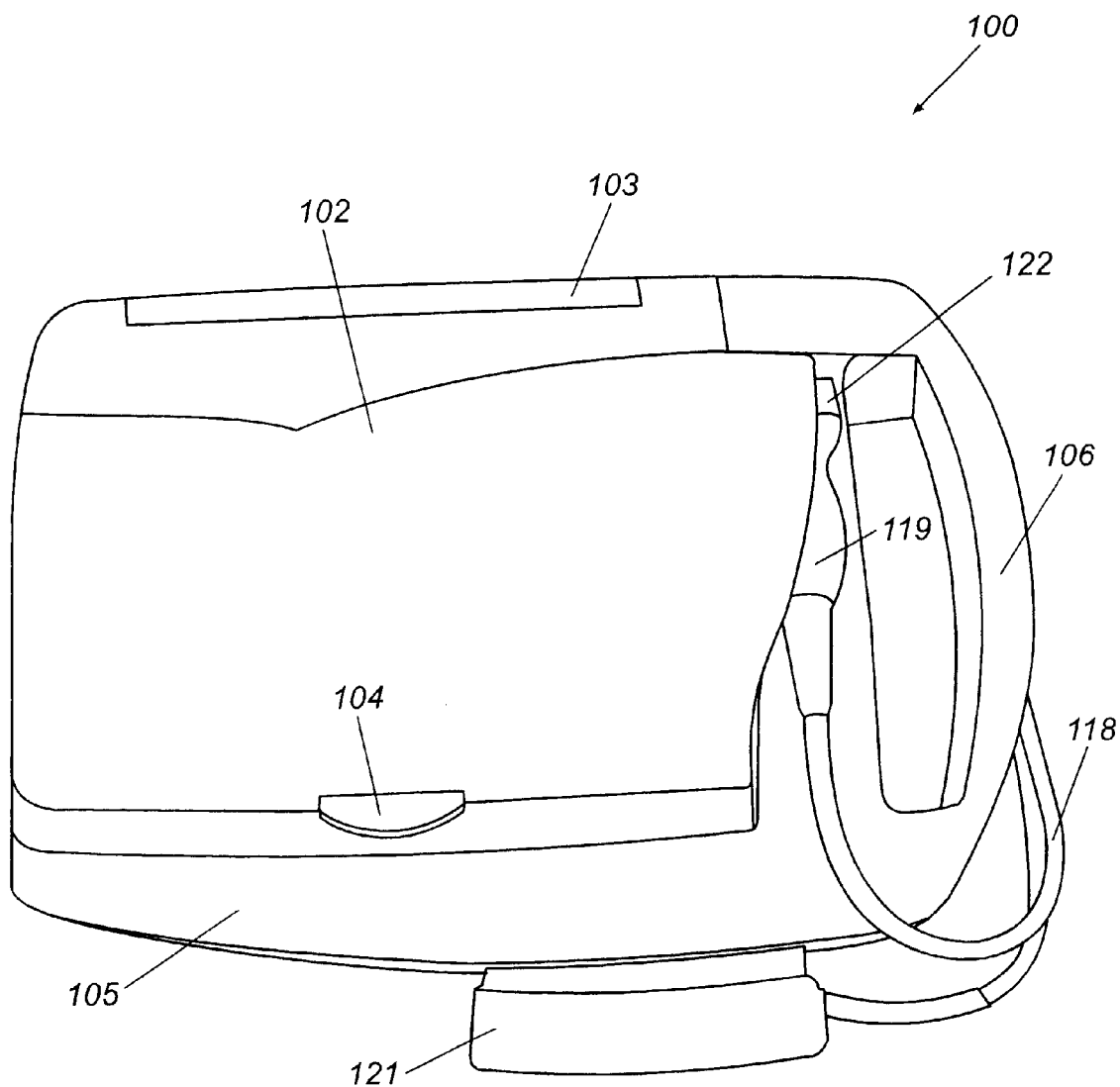
FIG. 9 is a top, perspective view of the ultrasound diagnostic device in accordance with an alternative embodiment.

FIGS. 9–12 are directed to an alternative embodiment of the ultrasound device on the present invention. The ultrasound device 100 shown in FIG. 9 is designed to enable images to be stored in a standard format, such as the JPEG (Joint Photographic Experts Group) format, for example, on a compact flash storage device of the ultrasound device 100 so that the images can be easily archived, viewed, printed, etc., by the user. This feature of the ultrasound device 100 renders it particularly suitable for home use.

In the past, many ultrasound systems have provided digital image storage by networking images to a personal computer (PC) or server, or by storing images to a removable storage media, such as a magneto-optical disk. Although these solutions do offer digital storage and generally preserve image quality, they generally are not cost-effective or easy to use. Networks, servers and disk drives are expensive and often require specialized personnel to operate and administer. Additionally, the images are typically stored in a format specific to ultrasound technology, such as DSR (Digital Storage and Retrieval) or DICOM (Digital Imaging and Communications in Medicine), which are specifically designed for the medical community. Consequently, special software is required to view these images off-line. The special software is typically expensive and may require specialized personnel or training to operate.

Thus, the ultrasound device 100 is capable of digitally storing ultrasound images in a format that can be easily archived, transferred to a PC, printed, viewed, e-mailed, etc., and which does not require specialized training or specialized hardware and/or software to utilize. The ultrasound device 100 is equipped with an "image frame storage" control that causes the ultrasound system to enter a frozen imaging mode and then store the currently displayed image to the compact flash card in one of the aforementioned standard image formats. As stated above, preferably the images are stored in the JPEG format.

While the image data is being stored, preferably an "image frame storage in progress icon" appears on the display screen of the ultrasound device. The icon preferably displays the number of still-frame images that can be stored on the card after the current image is stored. When the storage operation is complete, the icon disappears. An "image frame compression level" indicator is also displayed which indicates the amount of compression that has been used to store the file.

The JPEG format is preferred due to its universal acceptance and the ubiquity of PC software to manager JPEG files. PCs and Internet browsers typically support reading JPEG files. Therefore, the customer or user is not required to purchase special software to enable images to be accessed and viewed. Images can also be stored in the DICOM format so that systems that are equipped with the special software required for this format can also access and view the stored images. The storage features and other features relating to the electrical control circuitry of the ultrasound device will be discussed in detail below with reference to FIG. 5.

Before discussing the electrical control circuitry of the ultrasound device 100, an overall discussion of an ultrasound device 100 with which the electrical control circuitry can be used will be provided. It should also be noted that the electrical control circuitry discussed below can also be used with the ultrasound device 10 discussed above with reference to FIG. 1. However, it should be noted that the electrical control circuitry of the present invention is not limited with respect to the type of ultrasound device with which it is implemented.

The ultrasound diagnostic device 100 shown in FIG. 9 is approximately 10½ inches long, approximately 8 inches wide and approximately 2¾ inches thick, although those skilled in the art will understand that it is not limited to these exact dimensions. The weight of the device 100 is less than 7 pounds, including the electrical control circuitry, the battery pack, and the transducer assembly. The device 100 is similar in design to a laptop computer. The device 100 comprises a console portion 105 and a display portion 102. To open the device 100, the user opens the display portion 102 by unlatching and lifting up on the tab 104 located on the display portion 102. The display portion 102 is coupled by a hinging mechanism 103 to the console portion 105 so that when the user lifts up on the display portion 102, it rotates upwards (i.e., away from the console portion 105). The hinging mechanism 103 preferably is similar to hinging mechanisms typically used with laptop computers currently available on the market.

A handle 106 is integrally connected to the console portion 105 to allow the device 100 to be easily carried by hand. A transducer assembly is removably connected by a connector 121 to the ultrasound diagnostic device 100 and comprises a transducer cable 118, a transducer handle 119, and a transducer 122. The connector 121 comprises a latch (not shown) which engages a mating mechanism (not shown) comprised in the console portion 115. Preferably, the transducer handle 119 is small enough to fit comfortably in the palm of the hand of the user so that it can be easily manipulated by the user.

The connector 121 enables different types of transducer assemblies to be implemented with the ultrasound diagnostic device 100. Depending on the bodily feature being imaged, different transducer assemblies can be utilized with the ultrasound diagnostic device 100. The user can easily unplug one type of transducer assembly and easily plug another transducer assembly into the receptacle of connector 121. Of course, each transducer assembly must be adapted to mate with the connector 121. This provides the ultrasound diagnostic device 10 with great flexibility with respect to its applications, as will be understood by those skilled in the art.

Figure 10:
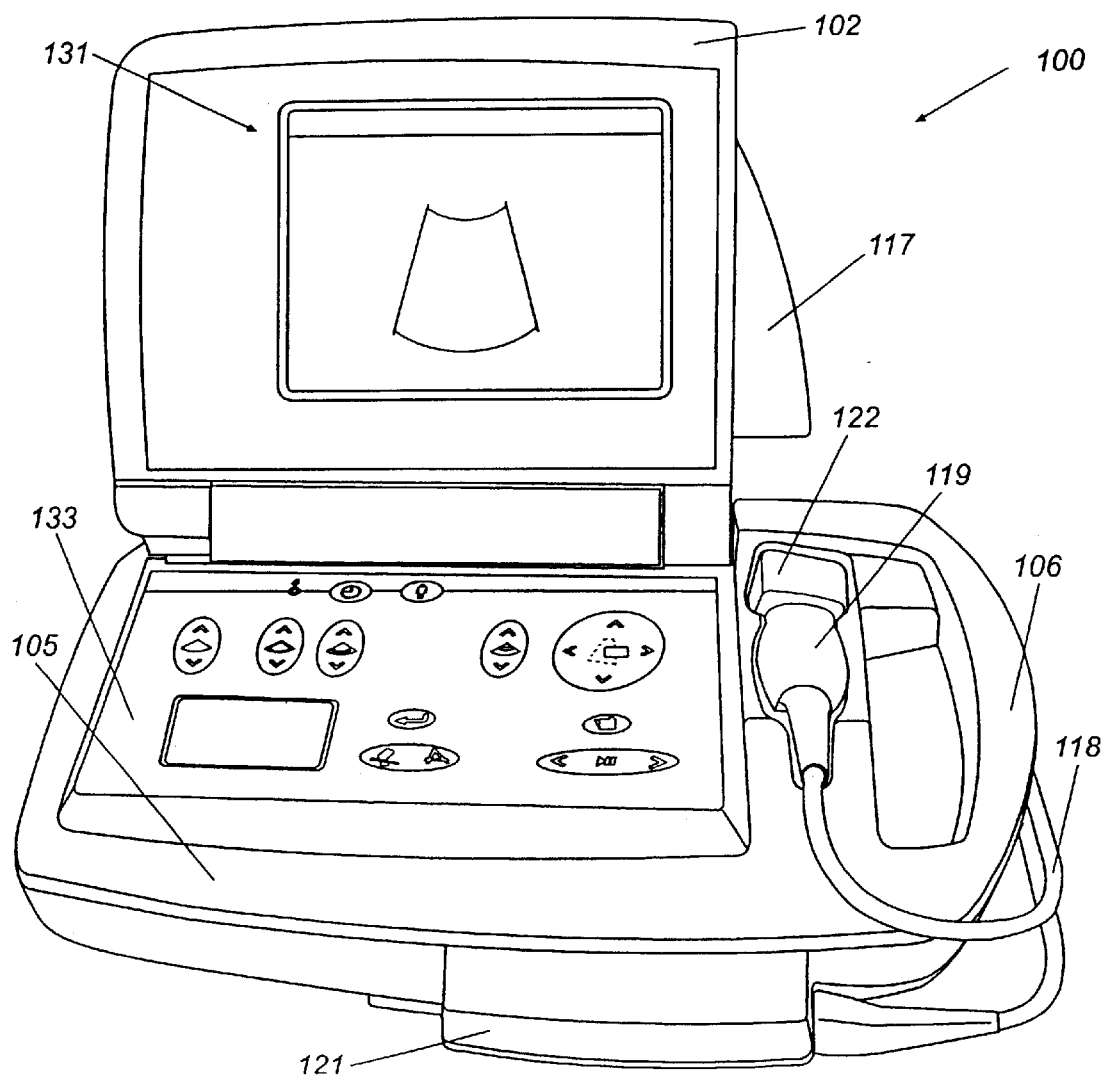
FIG. 10 is front, perspective view of the ultrasound diagnostic device shown in FIG. 9 with the display screen placed in a viewing position.

FIG. 10 illustrates the ultrasound diagnostic device 100 with the display portion 102 placed in a viewing position. Preferably, the display screen 131 comprised by the display portion 102 is a liquid crystal display (LCD) screen. The console portion 105 comprises a small control panel 133 having various input keys, which preferably have icons on them. By using icons on the keys, a single control panel in the console portion 105 can be used in different countries around the world because the icons preferably are selected so that their meanings are well known to those who perform ultrasound diagnostic imaging tasks, as will be understood by those skilled in the art.

Preferably, the display portion 102 and the console portion 115 are comprised of cast metal and molded plastic to provide the ultrasound diagnostic device 100 with a rugged encasement. The ultrasound diagnostic device 100 is designed to withstand external impact resulting from, for example, dropping the device 100 or collisions between the device 100 and external objects. Furthermore, the ultrasound diagnostic device 100 also folds such that when it is not in use, the display screen 131 and the control panel 133 are protected from external forces. The transducer connector 121 is also designed of the same or similar types of materials so that it can also withstand shocks from external forces. A flange 117 helps hold the transducer portions 119 and 122 in place when the device 100 is not in use and protects these portions of the transducer assembly.

Figure 11:
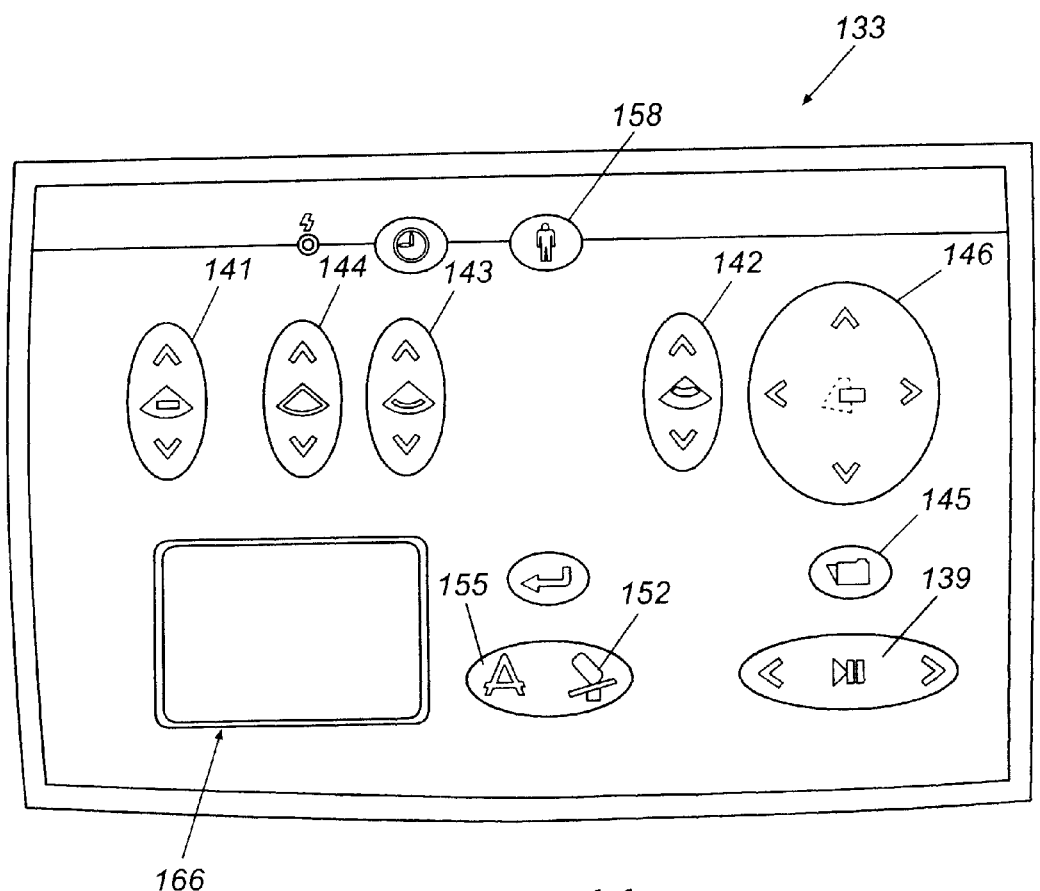
FIG. 11 is a top view of the control panel of the ultrasound diagnostic device of FIG. 9, which illustrates the icons located on the input keys.

FIG. 11 is a top view of the control panel 133 of the ultrasound diagnostic device 100. All system controls are preferably "one button-one function", i.e., each key corresponds to a command that tells the CPU to perform a particular function. The keys preferably are logically and ergonomically grouped in such a manner that they can be easily identified and so that their meanings are self-explanatory. It should be noted that the control panel 133 is not limited to the particular buttons and icons shown in FIG. 11.

Preferably, all of the buttons are membrane keys. The button 139 is actuated by the user in order to freeze an image being displayed on the display monitor. For example, if an image is being displayed on the display monitor at a rate of 130 frames per second, activating the stop button 139 will freeze the last image that was being displayed when the button 139 was activated. The electrical control circuitry will cause this image to continue to be displayed either for a predetermined period of time or until the button on the console is reactivated. In the exemplary embodiment, when the button 139 is activated a second time (i.e., toggled), the device 100 will resume displaying the images in real time as they are acquired. The shape of the freeze button 139 is a universal symbol, which facilitates ease of use of the ultrasound diagnostic device by the user.

The pie slice shaped icon 141 which has "cm" in the center of it and arrow heads above and below it, represents the image sector, which is commonly referred to as a B-mode image sector, seen by the user on the display monitor. The button 141 is used to adjust the depth of the image being displayed. For example, if the depth of the image being displayed is 8 centimeters and the user desires to view an image at a depth of from 0 to 4 centimeters in the body, the user depresses the button 141 at the location of the up arrow. The display monitor will display information corresponding to the depth of the image being displayed.

The three buttons 142, 143 and 144 are gain variance control buttons. The user uses these buttons to control what is commonly referred to as time gain compensation (TGC). The electrical control circuitry preferably comprises a time gain amplifier (not shown) which varies gain with respect to time. As acoustical energy is propagated into the body by the transducer, the body absorbs some of the energy, while some of the energy is reflected back out of the body and received by the transducer. The strength of this echo will vary depending on the distance that the object that caused the echo is away from the transducer. Therefore, in many cases it is desirable or necessary to amplify the echoes. The button 144 is used to control the overall gain of the image being displayed. To decrease the gain, the user depresses the button 144 at a location on the down arrow. To increase the gain, the user depresses the button 144 at a location on the up arrow.

The button 143 is used to increase and decrease the gain of echoes that correspond to targets in the top section of the displayed image. This section of the displayed image corresponds to targets that are relatively close to the transducer. The button 142 is used to increase and decrease the gain of color flow. Button 145 has an icon on it that represents a folder. This can be used to store, for example, an image frame that has been frozen by activating the freeze button 139. The button 146 is utilized to position a superimposed Color Flow Doppler image over the B-Mode image being displayed on the display monitor. In ultrasound imaging, colors are utilized to represent velocity. The well-known Doppler effect is utilized to determine the velocity of the target being imaged and to encode the image data with colors. For example, if blood is flowing towards the transducer, the blood is typically represented in yellow or red on the display monitor, depending on the velocity of the blood. If blood is flowing away from the transducer, it is typically displayed in blue on the display monitor. For example, if the user is viewing a vessel in which all the blood is flowing away from the transducer, the vessel would be colored blue. If the user is viewing a vessel in which all of the blood is moving towards the transducer, the vessel would be colored yellow or red, depending upon the velocity.

The button 146 allows an image sub-sector that is colored to be superimposed over the B-mode image sector being displayed. The B-mode image may be, for example, a sector image that is 90 degrees in width. The button 146 allows the user to shift the superimposed color sector to any location over the B-mode image sector by using the arrow keys. The button 148 is used to turn the color flow on and off and to select the type of color flow to be displayed.

The functions of the buttons 152, 155 and 158 will be described with respect to an imaging example in which ultrasound diagnostic device 100 is used to obtain an image of a baby's head. As the transducer is being used to acquire the image, if the freeze button 139 is depressed, the image on the display monitor will be frozen. The button 155 having the icon of a pair of calipers thereon is then depressed, which causes a cross mark similar to a cursor to be displayed on the display monitor. The distance between the cross mark location and the transducer (the depth of the cross mark) is displayed. The user may then move the cross mark around with his or her fingertip by using the touch-sensitive pointing device 166. When the cross mark has been placed by the user over the point of interest in the image, the user depresses the caliper button 155 again. This causes the first cross mark to be anchored and a second cross mark to be displayed on the display monitor. The user then moves the second cross mark until it has been placed over another point of interest on the image. As the second cross mark is moved, the distance between the two cross marks will be displayed on the display monitor in centimeters and fractions thereof.

Selecting the Image Frame Storage Control mode (button 145) causes the ultrasound device to enter Frozen Imaging mode (if it isn't already frozen), and then store the currently displayed image to the compact flash card in JPEG format (or other standard format). While the storage is in progress, an "Image frame storage in progress" icon (not shown) appears on the display screen. The icon displays the number of still frame images that can be stored on this card after this image. When the storage operation is complete, the icon is removed. Also displayed on the display screen is an Image frame compression level (not shown). This is an indicator of how much compression was used when storing the file.

Each time the caliper button 155 is depressed, another cross mark will be displayed up to a maximum of four cross marks. This enables the user to measure up to two distances between objects in the body being displayed. If the user does not like where one of the cross marks is anchored, the user can depress the erase button 152, which will cause the most recent cross mark to be erased. Button 158 is used to allow the user to enter identification information about the patient.

Figure 12:
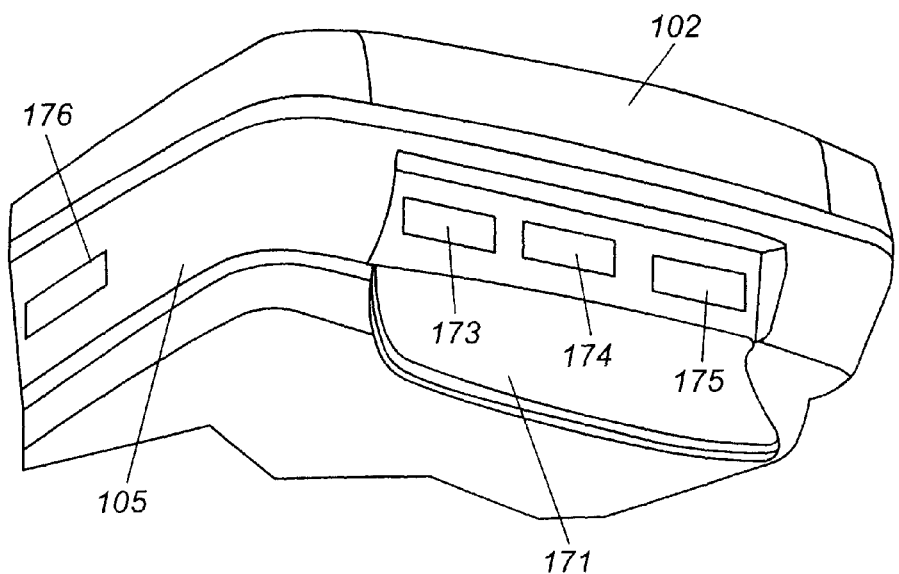
FIG. 12 is a rear, perspective view of the ultrasound diagnostic device shown in FIG. 9.

FIG. 12 is a rear perspective view of the ultrasound diagnostic device shown in FIG. 9. The rear end of the ultrasound diagnostic device 100 is similar to that of the ultrasound device 10 shown in FIG. 7, with the exception that the connections for the strap are not needed (and therefore are not shown) for the ultrasound device 100. The ultrasound device 100 also has a rear cover panel 171 that is similar or identical to that of ultrasound device 10, (which can be opened and closed to allow various data storage and transmission devices to be connected into the ultrasound diagnostic device via ports 173, 174, 175 and 176. Ports 173, 174, 175 and 176 serve identical purposes to ports 73, 74, 75, 75 and 76, respectively, described above with reference to FIG. 7. Therefore, a detailed discussion of these ports will not be provided herein. Port 176 preferably is designed to receive a compact flash card, which can be used as a mass storage device for the ultrasound device 100. Use of the compact flash card enables large quantities of imaging data to be downloaded from the ultrasound device 100. One of the advantages of using a compact flash card as the mass storage device 225 is, in addition to the capability of storing large amounts of data, they are very small in size, typically on the order of one or two square inches.

Figure 13:
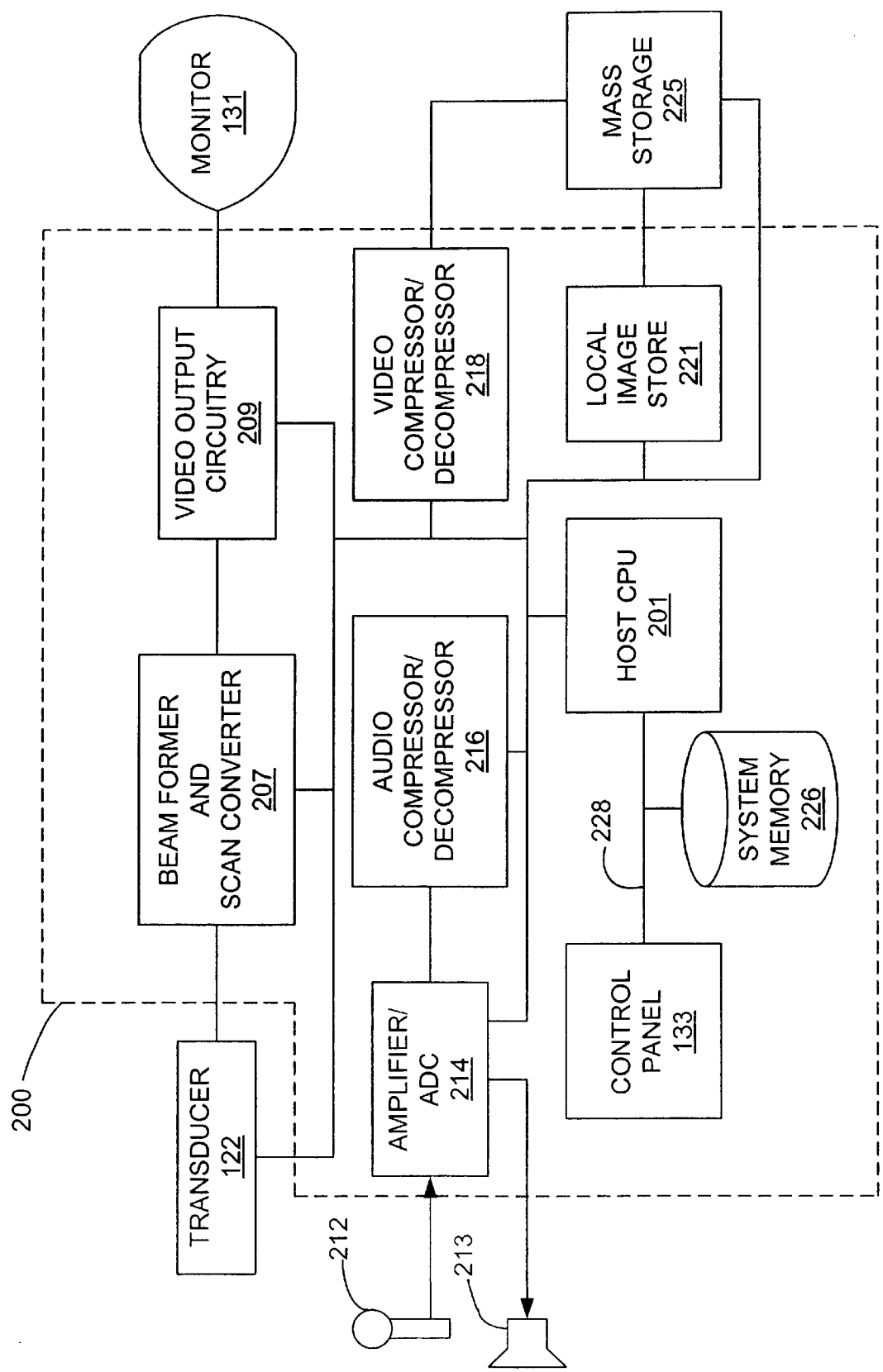
FIG. 13 is a block diagram of the electrical control circuitry and software of the ultrasound diagnostic devices of the present invention.

FIG. 13 is a block diagram of the electrical control circuitry of the present invention in accordance with the preferred embodiment. As stated above, the electrical control circuitry 200 is suitable for use with both of the ultrasound devices 10 and 100. The electrical control circuitry 200 is electrically coupled to the transducer 122, to the display monitor 131 and to a mass storage device 225. Preferably, the electrical control circuitry 200 is also electrically coupled to an audio input device 212 (e.g., a microphone) and to an audio output device 213 (e.g., a speaker).

The ultrasound image acquisition component is comprised of a beam former/scan converter 207 and a transducer 122. The beam former/scan converter component 207 generates electrical signals necessary to cause transducer 122 to form an acoustic beam by launching a shaped acoustic wave. Reshaped acoustic waves which are returned from discontinuities in the body are returned to the transducer, and reconverted into electrical signals. These signals are processed by the beam former/scan converter component 207 and stored in the appropriate pixels in the appropriate frame of local image storage device 221. As the acoustic beam is steered in different directions by the beam former/scan converter component 207 and the transmission/reception process is repeated by beam former/scan converter component 207, different pixels in the selected frame of local image storage device 221 are filled in with image data.

When all of the specified acoustic lines have been shot, a cross-sectional map of the property of the body being examined, such as, for example, tissue velocity, or acoustic impedance, the corresponding digital image data will have been placed in the specified frame of local image storage device 221. The necessary sub-functions performed by a beam former/scan converter component 207 are well known to those skilled in the art, and are documented in many publicly available books and articles. A readily available example of such a description may be found in Chapters 3, 4 and 6 of a book entitled *Diagnostic Ultrasound Principles, Instruments, and Exercises*, Third Edition, by Frederick W. Kremkau, PhD., WB Saunders Company, 1989, which is incorporated herein by reference.

Each page of the local image storage device 221 contains the data for one frame that is to be displayed on the display monitor 131. This memory device 221, which preferably is a fast semiconductor memory device, may contain many frames or as few as two frames, but typically less than 100 frames, due to the cost of this type of memory device. An example of a semiconductor memory device that is suitable for implementation as the local image storage device 221 is a Synchronous DRAM (dynamic random access memory) integrated circuit chip, such as, for example, an NEC 4516161-10 DRAM integrated circuit chip, manufactured by NEC Corporation. This particular memory device is capable of storing 4 megabytes of 16 bit words. Preferably, the local image storage device 221 is comprised of a plurality of these integrated circuit chips. However, those skilled in the art will understand that the present invention is not limited with respect to the amount of memory comprised by the local image storage device 221 or with respect to the type of memory device utilized for this purpose.

The video output circuitry 209 formats the data in accordance with a predetermined horizontal and vertical synchronization technique appropriate for the display monitor 131. The video output circuitry also translates the data into either color data or black-and-white data, depending upon the data stored in local image storage device 221, and the requirements of the display monitor 131. Graphics and text may be generated by the host CPU 201 and added to the image frames by the video output circuitry 209.

The host CPU 201 executes programs stored in system memory 226 and receives commands from the control panel 133 in response to commands entered by a user (not shown) on the control panel 133. The CPU 201 processes these commands in a manner dictated by one or more programs being executed by the CPU 201. Many of these commands correspond to operations to be performed on the ultrasound image, as were discussed above with reference to FIG. 11. The host CPU 201 translates these commands into control data to be output to the video output circuitry 209 and/or to the beam former/scan converter component 207. The operations of the beam former/scan converter component 207 and of the video output circuitry 209 are controlled via these commands.

The beam former/scan converter component 207, the local image storage device 221, and the video output circuitry 209 operate in conjunction with one another in response to the commands received from the CPU 201 to perform the operations on the ultrasound image. The manner in which these components cooperate with one another to perform these operations is well known to those skilled in the art. Therefore, in the interest of brevity, a detailed discussion of the operations of these components will not be provided herein.

Several video output circuitry components are available on the market that are suitable for performing the formatting and translation functions of the video output circuitry 209. Similarly, a plurality of transducers are available on the market that are suitable for performing the functions of the transducer 122. Preferably, the transducer 22 is a 2.5 megahertz phased array sector transducer sold by Agilent Technologies, Inc. Often times, it is desirable to store many seconds of the ultrasound image. For example, it may be desirable to capture many segments of heart activity. As stated above, the local image storage device 221 typically is too small for this purpose. The local image storage device 221, due to the high cost of fast, semiconductor memory, generally holds anywhere from two to one hundred pages of image data. This problem is solved by utilizing an additional mass storage device 225, which preferably utilizes Compact Flash technology, as discussed below in more detail.

To further reduce the cost of mass storage per stored page, image data from local image storage device 221 preferably is routed through video compressor/decompressor 218. As image data is routed from image memory 221 to mass storage device 225, it is compressed. As data is routed from mass storage device 225 to local image storage device 221, it is decompressed. Compression ratios of ten or fifteen to 1 are achievable with little or no degradation of the image. However, the invention is not limited to any particular compression ratios.

The images that are stored on the compact flash card 225 preferably are stored in JPEG format. By utilizing compact flash technology and storing images in the JPEG format, the images can be easily archived, transferred to a PC, printed, viewed, emailed, incorporated into presentations, etc. Suitable compact flash technology for use with the present invention is produced by SanDisk Corporation. This technology is readily available to consumers and is relatively inexpensive. Very low cost compact flash interfaces are available for PCs, and some printers have built-in compact flash interfaces. Additionally, this technology is easy for consumers to use and requires no specialized personnel or training to operate.

Additionally, by storing images in JPEG format, no specialized software is required to access and view the images. Standard desktop PCs come with software that can read JPEG files, so users can easily access their images without special equipment, training, or personnel and at no additional expense. Of course, those skilled in the art would understand that images could be stored in other standard formats, such as the TIFF format, for example. Preferably, the Video Compressor/Decompressor component 218 that provides the compression/decompression functions in accordance with the JPEG or other standard imaging format is implemented in software that is executed by the CPU 201. However, these functions could also be performed in hardware or a combination of hardware and software, as will be understood by those skilled in the art.

The JPEG format provides video compression and decompression to be performed using standard JPEG algorithms. A wavelet compression algorithm is another example of a compression algorithm that may also be used for this purpose. JPEG compression and decompression algorithms can be performed in hardware using a particular integrated circuit or in software being executed on the CPU 201, which preferably is a microprocessor. Wavelet compression algorithms can also be performed in hardware and/or software. A suitable video integrated circuit chip for performing video compression and decompression is produced by Zoray Corporation and is marketed as model number ZR36050. This particular video integrated circuit chip utilizes the JPEG compression standard. With respect to audio compression and decompression, several standard compression/decompression algorithms are available on the market. For example, a computer program known as Microsoft ADPCM Codec, which is commonly supplied with versions of Windows by Microsoft Corporation, is suitable for performing audio compression/decompression.

The compact flash technology utilized also enables files to also be stored in DICOM format. Software executed by the CPU 201 works in conjunction with the compact flash card to enable images to be stored thereon in this format. Therefore, systems that are equipped with the special software required for this format can also access and view the stored images downloaded from the ultrasound device 100 to the compact flash disk 225. Therefore, although the ultrasound diagnostic device 100 preferably is designed for home use by a patient, it is not limited to this use. It is also suitable for use in healthcare facilities by persons with specialized training, as will be understood by those skilled in the art.

The ultrasound diagnostic device 100 comprises a network connection to enable the electrical control circuitry 200 to be interfaced with a network. This type of connection allows the image information stored in the local image store 221 and/or in the mass storage device 225 to be downloaded directly onto a network. As stated above with reference to FIGS. 7 and 12, the ultrasound diagnostic device 100 preferably comprises a port 173 that functions as a network connection to allow the user to insert, for example, an Ethernet card (not shown) into the network connection port 173 to allow the image data to be downloaded directly onto a network. An optical link, such as, for example, an Infrared link (port 174), may also be used to allow data to be downloaded from and loaded into the ultrasound diagnostic device 100.

In accordance with the preferred embodiment of the present invention, the electrical control circuitry 200 allows the user to generate audio files, which are appended to the ultrasound images to which they correspond. To accomplish this goal, the console portion 105 of the ultrasound diagnostic device 100 has an audio input port (not shown) adapted to allow an audio input device 212, such as a microphone, to be coupled to the electrical control circuitry

200. An amplifier and analog-to-digital converter component 214 receives analog signals from the audio input device 212 and performs amplification and analog-to-digital conversion to obtain a digital audio image. The host CPU 201 may then cause the digital audio image information to be compressed by audio compressor/decompressor 216 component and stored in a memory device, such as mass storage device 225.

The host CPU 201 also determines which audio information corresponds to the associated image information stored in the mass storage device 225. The host CPU 201 can perform this function in a plurality of manners, as will be understood by those skilled in the art. For example, the host CPU 201 can be programmed to tag the audio files with tags that associate the audio files with their respective image files. When the audio files and the image files are stored in the mass storage device 225, the tags that associate the audio files with the image files are also stored in the mass storage device 225. The audio files can be associated with the image files by using other techniques, such as, for example, storing audio files and image files in such a manner and in accordance with a predetermined ordering convention that the host CPU 201 can easily determine which files are audio files, which files are image files, and which image files are associated with which audio files. Those skilled in the art will understand how these tasks can be accomplished.

Under control of the host CPU 201, audio files may be read out of the mass storage device 225, decompressed, if necessary, in audio compressor/decompressor 216, and played back over audio output device 213. Also, the mass storage device 225 having the audio files and the image files stored therein may be removed from the ultrasound diagnostic device 100 and placed in an external read/write device (not shown) to allow the image information and the audio information to be downloaded from the mass storage device 225 to an external computer or memory device. As will be understood by those skilled in the art, the external computer will be configured with compact flash technology to allow the image files and audio files to be read off of the mass storage device 225, decompressed, if necessary, and presented to the user via appropriate output devices.

It should be noted that the audio compressor/decompressor component 216 may also be implemented in hardware, software executed by the CPU 201, or in a combination of hardware and software. Several audio and video compressors and decompressors are available on the market that are implemented entirely in hardware or entirely in software, or in a combination of hardware and software. An audio compression/decompression integrated circuit chip which is suitable for performing audio compression and decompression is manufactured by Cirrus Logic and is sold as model number CS4215.

The ultrasound diagnostic devices 10 and 100 of the present invention have been described with respect to particular embodiments, but are not limited to these embodiments. Those skilled in the art will understand that modifications may be made to the ultrasound diagnostic devices 10 and 100 that are within the scope of the invention.

What is claimed is:

1. An ultrasound diagnostic device for acquiring and processing ultrasound images, the device comprising:
   a transducer;
   a console portion having a plurality of input keys to enable a user to input commands and control circuitry that receives signals from the transducer and performs at least a portion of beamforming thereon and generates a display signal;
   a display portion mechanically coupled to the console portion and being positionably adjustable with respect to the console portion, the display portion having a display monitor that displays images based on the display signal from the console portion, wherein the images displayed on the display monitor are modified by the electrical control circuitry in response to one or more keys actuated by the user,
   wherein the console portion comprises a shell that defines a recess for receiving the transducer when the transducer is not in use, the recess being substantially coplanar with the console and not extending through the console, the transducer being substantially coplanar with the console when the transducer is received in the recess.

2. The ultrasound diagnostic device of claim 1, further comprising a transducer receptacle for selectable connection and disconnection of the transducer, the transducer receptacle being selectably connectable to a plurality of different transducer assemblies, each transducer assembly comprising a transducer connector which is adapted to be connected to the transducer receptacle.

3. The ultrasound diagnostic device of claim 1, wherein the display portion is coupled to the console portion with a hinging mechanism which allows the display portion to be rotationally adjusted with respect to the console portion.

4. The ultrasound diagnostic device of claim 3, wherein the console portion has a front-end, a back-end, a first side-end and a second side-end, the first and second side ends each having a shoulder strap attachment mechanism, the shoulder strap attachment mechanisms enabling a shoulder strap to be removably attached at first and second ends of the shoulder strap assembly to the first and second side ends, respectively, of the console portion, wherein when the display portion is in the closed position, the ultrasound diagnostic device is carryable over the user's shoulder by attaching a shoulder strap assembly to the shoulder strap attachment mechanisms and by placing the shoulder strap over the user's shoulder.

5. An ultrasound diagnostic device for acquiring and processing ultrasound images, the device comprising:
   a transducer;
   a console portion having a plurality of input keys to enable a user to input commands and control circuitry that receives signals from the transducer and performs at least a portion of beamforming thereon and generates a display signal;
   a display portion mechanically coupled to the console portion and being positionally adjustable with respect to the console portion, the display portion having a display monitor that displays images based on the display signal from the console portion, wherein the images displayed on the display monitor are modified by the electrical control circuitry in response to one or more keys actuated by the user,
   wherein the shoulder strap assembly further comprises a holster adapted to allow the user to store a transducer handle of the transducer assembly in the holster.

6. An ultrasound diagnostic device for acquiring and processing ultrasound images, the device comprising:
   a transducer;
   a console portion having a plurality of input keys to enable a user to input commands and control circuitry that receives signals from the transducer and performs at least a portion of beamforming thereon and generates a display signal;

a display portion mechanically coupled to the console portion and being positionally adjustable with respect to the console portion, the display portion having a display monitor that displays images based on the display signal from the console portion, wherein the images displayed on the display monitor are modified by the electrical control circuitry in response to one or more keys actuated by the user, wherein the console portion has a flange fixedly secured thereto, the flange being adapted to retain the transducer cable when the transducer cable of the transducer assembly has been wrapped about the flange, the flange maintaining the transducer cable adjacent the ultrasound diagnostic device.

7. The ultrasound diagnostic device of claim 4, wherein the shoulder strap assembly comprises a main strap portion, the main strap portion having a first end and a second end, the first end of the main strap portion having a front strap portion and a rear strap portion attached thereto, the second end of the main strap portion having a front strap portion and a rear strap portion attached thereto, the front and rear strap portions of the first and second ends of the main strap portion having ends adapted to be attached by fastening mechanisms to the side ends of the console portion, wherein when the main strap portion is disposed about the neck of the user, the front and rear strap portions are attached to the fastening mechanisms and to the main strap portion in such a manner that the control panel is fully supported in a substantially perpendicular position with respect to the user to enable the user to operate the ultrasound diagnostic device.

8. The ultrasound diagnostic device of claim 7, wherein when the ultrasound diagnostic device is over the user's shoulder, the front and rear strap portions are stored by securing the front and rear strap portions to the main strap portion.

9. The ultrasound diagnostic device of claim 8, wherein the front and rear strap portions and the main strap portion have a hook-and-loop material disposed thereon and wherein the front and rear strap portions are stored by securing the front and rear strap portions to the main strap portion using the hook-and loop material disposed on the main, front and rear strap portions.

10. An ultrasound diagnostic device for acquiring and processing ultrasound images, the device comprising:
   a transducer;
   a console portion having a plurality of input keys to enable a user to input commands and control circuitry that receives signals from the transducer and performs at least a portion of beamforming thereon and generates a display signal;
   a display portion mechanically coupled to the console portion and being positionally adjustable with respect to the console portion, the display portion having a display monitor that displays images based on the display signal from the console portion, wherein the images displayed on the display monitor are modified by the electrical control circuitry in response to one or more keys actuated by the user,
   wherein each of the keys has an icon corresponding to a command, wherein each icon is intended to inform the user of the function associated with the key having the icon thereon, wherein each command corresponds to a particular function to be performed by the electrical control circuitry.

11. The ultrasound diagnostic device of claim 1, wherein the console portion has an electric battery removably secured therein, the battery providing power to the electrical control circuitry and to the display monitor.

12. The ultrasound diagnostic device of claim 1, wherein the console portion further comprises a touch-sensitive control pad, the touch-sensitive control pad generating electrical signals in response to sensing pressure on the touch-sensitive control pad, the electrical signals generated by the touch pad corresponding to one or more input commands received by the electrical control circuitry, the electrical control circuitry modifying an image displayed on the display monitor in response to the electrical signals generated by the touch pad.

13. The ultrasound diagnostic device of claim 1, wherein the recess has a bottom surface which protects an underside of the transducer from damage when stored in the recess.

14. The ultrasound diagnostic device according to claim 13, wherein the recess does not extend through the console portion.

15. The ultrasound diagnostic device of claim 1, wherein the display portion comprises a projection that secures the transducer in the recess when the display portion is closed.

16. The ultrasound diagnostic device according to claim 15, wherein the projection extends at least partially over the recess such that when the transducer is stored in the recess, the projection at least partially protects an upper side of the transducer from damage.

17. An ultrasound diagnostic device for acquiring and processing ultrasound images, the device comprising:
   a transducer;
   a console portion having a plurality of input keys to enable a user to input commands and control circuitry that receives signals from the transducer and performs at least a portion of beamforming thereon and generates a display signal;
   a display portion mechanically coupled to the console portion and being positionally adjustable with respect to the console portion, the display portion having a display monitor that displays images based on the display signal from the console portion, wherein the images displayed on the display monitor are modified by the electrical control circuitry in response to one or more keys actuated by the user,
   wherein the console portion has a shell that defines a handle which enables a user to securely carry the ultrasound device with one hand.

18. An ultrasound diagnostic device for acquiring and processing ultrasound images, the device comprising:
   a console portion, the console portion comprising means for inputting commands into the ultrasound diagnostic device, the console portion comprising means for receiving electrical signals from the control panel, the electrical signals corresponding to commands entered by the user on the means for inputting commands, the console portion comprising means for processing the electrical signals to produce image control commands;
   a display portion mechanically coupled to the console portion by a means for coupling the display portion to the console portion, wherein the means for coupling enables the display portion to be positionally adjusted with respect to the console portion, the display portion comprising a means for displaying ultrasound images, wherein the ultrasound images displayed may be modified by the means for processing in response to one or more keys of the control panel being actuated by the user;
   means for converting electrical signals into acoustical pulses intended to be propagated into a body, wherein the means for converting electrical signals into acoustical pulses receives the electrical signals to be converted into acoustical signals from the means for processing; and means for converting acoustical pulses reflected out of the body into electrical signals, wherein the means for converting acoustical pulses into electrical signals outputs the electrical signals to the means for processing, and wherein the means for processing causes an image to be displayed on the means for displaying ultrasound images, the ultrasound images displayed corresponding to the acoustical signals reflected out of the body, wherein the ultrasound diagnostic device weighs less than approximately 6 pounds, wherein the ultrasound diagnostic device comprises means for storing the transducer cable in an abutting relationship with said console portions.

19. The ultrasound diagnostic device of claim 18, wherein the means for coupling couples the display portion to the console portion in a hinging relationship which allows the display portion to be rotationally adjusted with respect to the console portion, and wherein the ultrasound diagnostic device comprises a means for locking the display portion and the console portion together in a closed position in which the means for displaying is positioned adjacent the control panel of the console portion.

20. The ultrasound diagnostic device of claim 19, wherein the console portion has a front-end, a back-end, a first side-end and a second side-end, the first and second side-ends each having a means for removably attaching a shoulder strap thereto, wherein when the display portion is in the closed position, the user can carry the ultrasound diagnostic device over the user's shoulder by attaching a shoulder strap to the means for removably attaching the shoulder strap and by placing the shoulder strap over the user's shoulder.

21. The ultrasound diagnostic device of claim 20, wherein said means for converting acoustical signals into electrical signals and said means for converting electrical signals into acoustical signals are comprised in a transducer, the transducer being attached to a handle which allows the transducer to be manipulated by a user, the transducer handle being attached to the ultrasound diagnostic device by a transducer cable, wherein the shoulder strap assembly comprises a holster adapted to allow the user to store the transducer handle in the holster.

22. The ultrasound diagnostic device of claim 20, wherein the shoulder strap comprises a main strap portion, the main strap portion having a first end and a second end, the first end of the main strap portion having a front strap portion and a rear strap portion attached thereto, the second end of the main strap portion having a front strap portion and a rear strap portion attached thereto, the front and rear strap portions being attached to the side ends of the console portion, wherein when the main strap portion is disposed about the neck of the user, the control panel is fully supported in a substantially perpendicular position with respect to the user to enable the user to operate the ultrasound diagnostic device.

23. The apparatus of claim 22, wherein when the ultrasound diagnostic device is carried by the user over the user's shoulder, the front and rear strap portions are secured to the main strap portion by a means for securing the front and rear strap portions to the main strap portion.

24. The apparatus of claim 23, wherein the means for securing the front and rear strap portions to the main strap portion is a hook-and-loop material disposed on the main, front and rear strap portions.

25. A portable ultrasound imaging device comprising:

a transducer;

a display;

control circuitry that outputs an output signal to the transducer causing the transducer to output ultrasound signals toward a subject and receives input signals corresponding to echoes of the ultrasound signals from the transducer, the control circuitry using the input signals to create display signals that cause the display to display an image representative of the subject; and a clam-shell case that integrates the display and the control circuitry, the clam-shell case having first and second portions which are rotatably coupled along first respective edges thereof, the first and second portions being rotatably adjusted with respect to each other.

26. The device of claim 25, wherein the portable ultrasound imaging device weighs less than 10 pounds.

27. The device of claim 25, wherein the shell defines a recess for receiving the transducer when the transducer is not being used.

28. The device of claim 27, wherein the shell has a projection that secures the transducer in the recess when the shell is closed.

29. The device according to claim 27, wherein the recess is substantially coplanar with the console and not extending through the console such that the transducer is received in the recess, the transducer is substantially coplanar with the console.

30. The device according to claim 26, wherein the recess has a bottom surface which protects the transducer from damage when stored in the recess.

31. The device of claim 25, wherein the shell defines a handle.

* * * * *